United States Patent [19]

Kohno et al.

[11] Patent Number: 5,149,503
[45] Date of Patent: Sep. 22, 1992

[54] APPARATUS FOR MEASURING HEMOGLOBIN CONCENTRATION AND OXYGEN SATURATION THEREOF

[75] Inventors: Hiromasa Kohno, Kanagawa; Hiroaki Honda, Naha; Masahiro Nudeshima, Kanagawa, all of Japan

[73] Assignee: Terumo Kabushiki Kaisha, Tokyo, Japan

[21] Appl. No.: 460,057

[22] PCT Filed: Jul. 22, 1988

[86] PCT No.: PCT/JP88/00742
§ 371 Date: Mar. 2, 1990
§ 102(e) Date: Mar. 2, 1990

[87] PCT Pub. No.: WO89/01144
PCT Pub. Date: Feb. 9, 1989

[30] Foreign Application Priority Data

Jul. 24, 1987 [JP] Japan .................................. 62-186135
Jul. 24, 1987 [JP] Japan .................................. 62-186136

[51] Int. Cl.$^5$ ........................ G01N 21/00; G01N 33/48
[52] U.S. Cl. .................. 422/82.05; 422/82.11; 356/39; 356/40; 356/41; 356/42; 356/445; 356/448; 436/66; 436/68; 436/164; 435/808
[58] Field of Search .............. 356/39, 40, 41, 42, 356/445, 448; 422/82.05, 82.11; 436/66, 68, 164; 435/808

[56] References Cited

U.S. PATENT DOCUMENTS

| | | | |
|---|---|---|---|
| 4,114,604 | 9/1978 | Shaw et al. | 356/41 X |
| 4,295,470 | 10/1981 | Shaw et al. | 356/41 X |
| 4,760,250 | 7/1988 | Loeppert | 250/205 X |
| 4,867,557 | 9/1989 | Takatani et al. | 356/41 |

FOREIGN PATENT DOCUMENTS

| | | | |
|---|---|---|---|
| 0240742 | 10/1987 | European Pat. Off. | 356/41 |
| 2251661 | 10/1987 | Japan | 356/40 |
| 2251662 | 10/1987 | Japan | 356/40 |
| 8606946 | 12/1986 | PCT Int'l Appl. | 356/41 |

OTHER PUBLICATIONS

Annals of Biomedical Engineering, vol. 14, No. 1, 1986, pp. 35-52, Pergamon Press Ltd., New methods for whole blood oximetry.

Primary Examiner—Robert J. Warden
Assistant Examiner—Stephanie Blythe
Attorney, Agent, or Firm—Frishauf, Holtz, Goodman & Woodward

[57] ABSTRACT

A light beam having a first wavelength ($\lambda_1$) is applied to the blood from a first light radiation section, while a light beam having a second wavelength ($\lambda_2$) is applied from second and third light radiation sections different in positions from the first radiation section and from each other to the blood and the respective reflected-light intensity ($I_1$, $I_2$, $I_3$) is detected. A first correction value (X) for correcting the reflected-light intensity ratio ($I_2/I_3$) is calculated by a first correction value operation section (40) and a second correction value ($C_1$) is calculated by a second correction value operation section (42) by use of this first correction value and the reflected-light intensity ($I_3$). The reflected-light intensity ratio ($I_1/I_2$) is corrected by use of this second correction value and an oxygen saturation in the blood is operated based on correlation function by use of the corrected reflected-light intensity ratio ($R_s$). The reflected-light intensity ratio ($I_2/I_3$) is corrected by the coefficient of correction thus operated and the hemoglobin concentration in the blood is operated based on correlation function by use of the reflected light intensity ratio thus corrected.

12 Claims, 23 Drawing Sheets

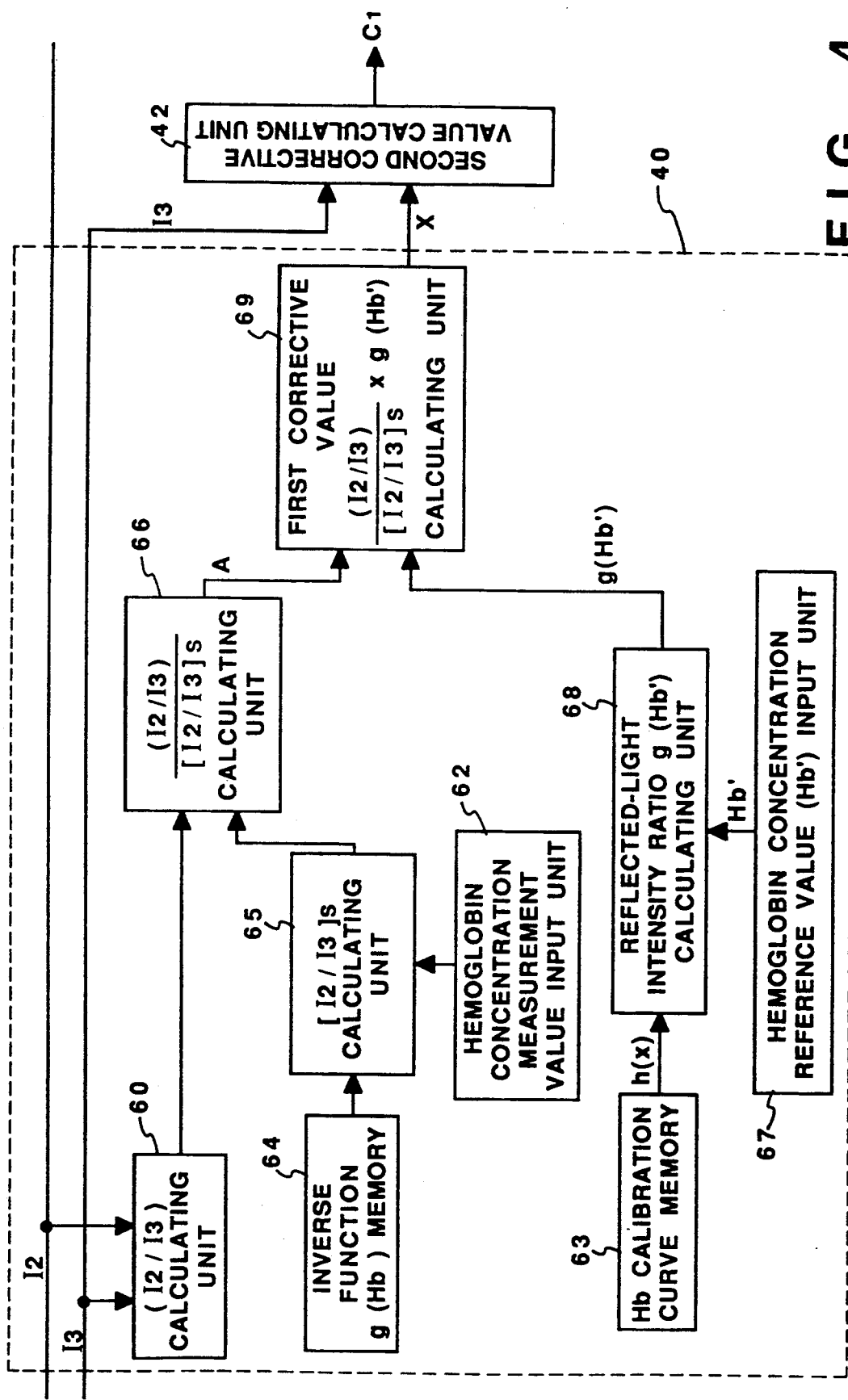
F I G. 4

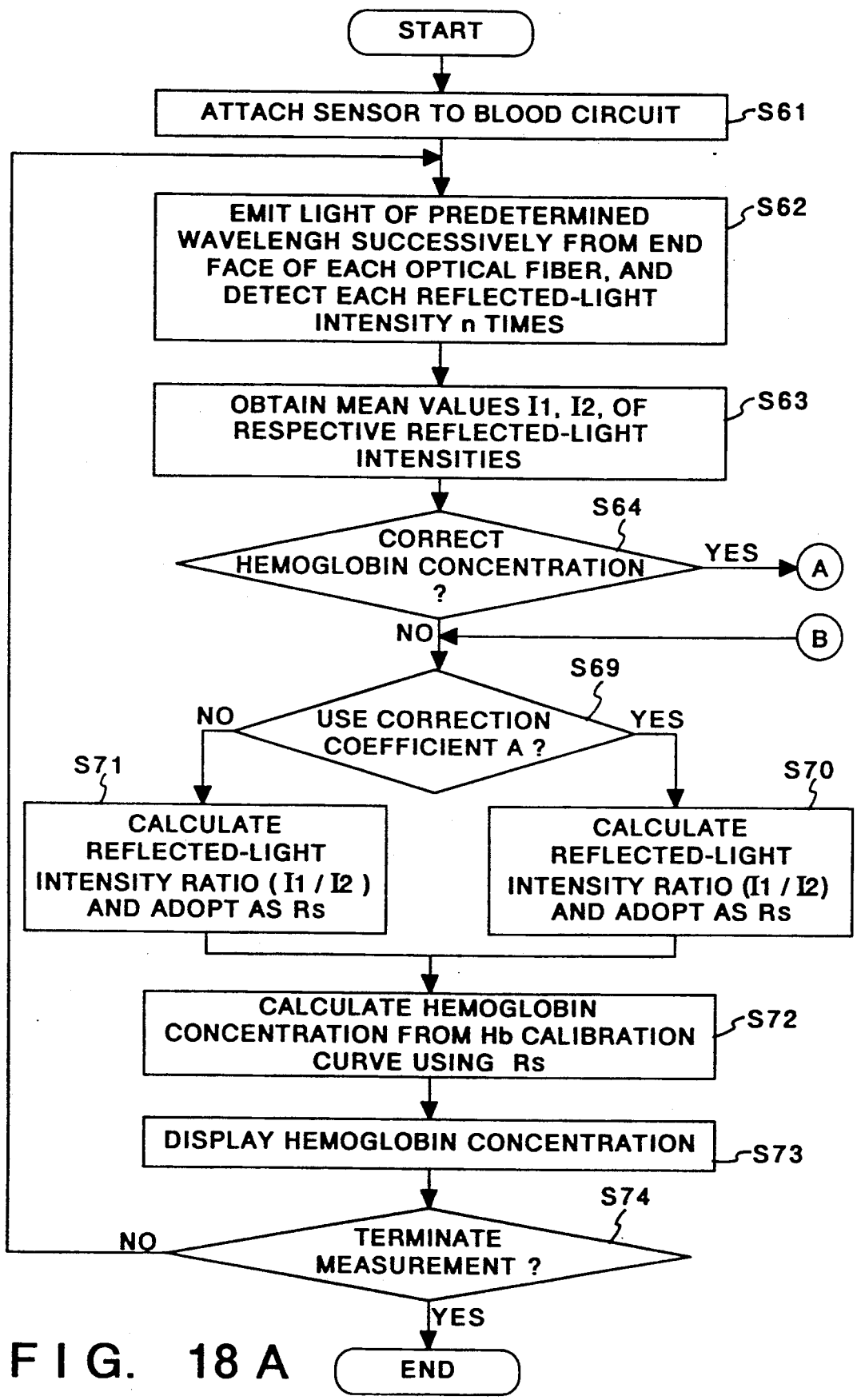
F I G. 18 A

APPARATUS FOR MEASURING HEMOGLOBIN CONCENTRATION AND OXYGEN SATURATION THEREOF

TECHNICAL FIELD

This invention relates to an apparatus for measuring hemoglobin concentration and hemoglobin oxygen saturation, which apparatus utilizes the extinction characteristics of hemoglobin in blood to measure the hemoglobin concentration in blood as well as the degree to which hemoglobin is saturated with oxygen.

BACKGROUND ART

Conventionally, measurement of hemoglobin concentration in blood is performed by hemolyzing sampled blood physically or chemically, introducing the sample to a cuvette and irradiating it with light of a specific wavelength, measuring the transmitted light and calculating the hemoglobin concentration using the Lambert-Beer law. With an apparatus and method for measuring the degree of oxygen saturation in hemoglobin contained in blood, the blood is irradiated with light having two wavelengths $\lambda_1$, $\lambda_2$, the intensity of the reflected light is measured, and the degree of oxygen saturation is determined from the following equation:

$$SO_2 = A + B \times (I_2/I_1)$$

where $I_1$, $I_2$ represent the intensities of the reflected light at the respective wavelengths $\lambda_1$, $\lambda_2$, and A, B are constants.

A problem with the above-described method of measuring hemoglobin concentration in blood is that continuous measurement is difficult since it is necessary to hemolyze the blood measured. In addition, a problem with the above-described method of measuring the degree of oxygen saturation of hemoglobin is that the results of measuring oxygen saturation are prone to error owing to the significant influence of physiological factors in blood, especially hematocrit value (the proportion of blood occupied by red blood cells). More specifically, the extinction (reflection) characteristics of blood vary depending upon absorption and scattering caused by pigments and particles contained in the blood. In particular, as shown in FIG. 13, light-absorption coefficient varies greatly depending upon the state of bonding between hemoglobin and oxygen and the wavelength of the irradiating light. Here $HbO_2$ represents oxygenated hemoglobin, Hbr represents reduced hemoglobin, and HbCO stands for carbomonoxyhemoglobin.

In the vicinity of a wavelength of 800 nm, $HbO_2$ and Hbr intersect and the light absorbancies are equal, as will be understood from these drawings. This wavelength is referred to as a point of equal absorption. This indicates a wavelength at which light absorbancy is not changed by the degree of oxygen saturation of hemoglobin.

FIGS. 14A and 14B are graphs in which the relationship between reflected-light intensity at wavelengths of 660 nm and 800 nm, respectively, and the degree of oxygen saturation is plotted while varying the hematocrit value (HCT) and hemoglobin (Hb) concentration. The blood sample used here was bovine blood.

In the case of the wavelength of 660 nm shown in FIG. 14A, the light absorbancy of oxygenated hemoglobin is small in comparison with that of reduced hemoglobin. Consequently, reflected-light intensity increases with a rise in the degree of oxygen saturation. In the case of the wavelength of 800 nm shown in FIG. 14B, it will be understood that a change in degree of oxygen saturation does not have much influence because this wavelength is the equal absorption point. Furthermore, it will be understood from FIGS. 14A, 14B that reflected-light intensity decreases with a decrease in the hematocrit value at each wavelength.

It should be noted that these measurements of reflected-light intensity are results obtained upon previously calibrating each reflected-light intensity to a predetermined value using a white reflector.

FIG. 15 illustrates the relationship between degree of oxygen saturation calculated using the foregoing equation and degree of oxygen saturation measured using an OSM2 hemoxymeter (manufactured by Radiometer) from measured values of reflected-light intensity at wavelengths 660 nm and 800 nm shown in FIGS. 14A, 14B, respectively. As a result, the degree of oxygen saturation calculated from the foregoing equation is profoundly influenced by the hematrocrit value in the region of low oxygen saturation, and a large error develops in the calculated value of oxygen saturation. Furthermore, in the prior art, the degree of oxygen saturation in blood cannot be measured accurately in continuous fashion without being influenced by the hematrocrit value.

DISCLOSURE OF THE INVENTION

An object of the present invention is to provide an apparatus for measuring degree of oxygen saturation, in which an accurate degree of oxygen saturation can be obtained without the influence of hematocrit value even in a region of low oxygen saturation.

Another object of the present invention is to provide an apparatus for measuring degree of oxygen saturation, in which the degree of oxygen saturation of hemoglobin can be measured continuously without the influence of the hematrocrit value.

A further object of the present invention is to provide an apparatus for measuring hemoglobin concentration, in which blood can be measured continuously and without hemolysis.

In order to solve the foregoing objects of the present invention, there is provided an apparatus for measuring the degree of saturation of oxygen in hemoglobin, comprising first light-irradiating means for irradiating blood with light of a first wavelength, second and third light-irradiating means for irradiating the blood with light of a second wavelength different from the light of the first wavelength, detecting means provided so as to be at different distances from the second light-irradiating means and third light-irradiating means for detecting intensities of light reflected from the blood irradiated with the light from the first light-irradiating means, second light-irradiating means and third light-irradiating means, first corrective value calculating means for calculating a first corrective value which corrects a ratio of the reflected-light intensity, which results from irradiation by the second light-irradiating means and is detected by the detecting means, to the reflected-light intensity, which results from irradiation by the third light-irradiating means and is detected by the detecting means, second corrective value calculating means for calculating a second corrective value using the first corrective value and the reflected-light intensity of light from the third light-irradiating means detected continuously by the detecting means, reflected-light intensity ratio correcting means for correcting, by using the second corrective value, a reflected-light intensity ratio of the reflected-light intensity of light from the first light-irradiating means detected continuously by the detecting means to the reflected-light intensity of light from the second light-irradiating means detected continuously by the detecting means, and oxygen saturation degree calculating means for calculating degree of oxygen saturation in blood based on a correlation function using the corrected reflected-light intensity ratio outputted by the reflected-light intensity ratio correcting means.

Further, the foregoing objects are attained by an apparatus for measuring the degree of saturation of oxygen in hemoglobin, comprising first light-irradiating means for irradiating blood with light of a first wavelength, second and third light-irradiating means for irradiating the blood with light of a second wavelength different from the light of the first wavelength, detecting means provided so as to be at different distances from the second light-irradiating means and third light-irradiating means for detecting intensities of light reflected from the blood irradiated with the light from the first light-irradiating means, second light-irradiating means and third light-irradiating means, first corrective value calculating means for calculating, from a reference value of hemoglobin concentration and a known value of hemoglobin concentration, a first corrective value for correcting a ratio of reflected-light intensities of light from the second and third light-irradiating means detected by the detecting means, second corrective value calculating means for calculating a second corrective value using the first corrective value and the reflected-light intensity of light from the third light-irradiating means detected continuously by the detecting means, reflected-light intensity ratio correcting means for correcting, by using the second corrective value, a reflected-light intensity ratio of the reflected-light intensity of light from the first light-irradiating means detected continuously by the detecting means to the reflected-light intensity of light from the second light-irradiating means, and oxygen saturation degree calculating means for calculating degree of oxygen saturation in blood using the corrected reflected-light intensity ratio outputted by the reflected-light intensity ratio correcting means.

Further, the foregoing objects are attained by an apparatus for measuring hemoglobin concentration, comprising first and second light-irradiating means for irradiating blood with light of a specific wavelength, detecting means provided so as to be at different distances from the first light-irradiating means and second light-irradiating means for detecting intensities of light reflected from the blood irradiated with the light from the first and second light-irradiating means, corrective coefficient calculating means for calculating a corrective coefficient which corrects a ratio of the reflected-light intensity of light from the first light-irradiating means to the reflected-light intensity of light from the second light-irradiating means, these light intensities being detected by the detecting means, reflected-light intensity ratio correcting means for correcting, by using the corrective coefficient, a reflected-light intensity ratio of the reflected-light intensity of light from the first light-irradiating means detected continuously by the detecting means to the reflected-light intensity of light from the second light-irradiating means, and hemoglobin concentration calculating means for calculating hemoglobin concentration in blood based on a correlation function using the corrected reflected-light intensity ratio outputted by the reflected-light intensity ratio correcting means.

In accordance with the present invention, the light-irradiating means can be reduced in size by making common use of both a light-emitting source and a light-irradiating unit.

In accordance with the present invention, a portion in contact with the blood can be completely insulated by connecting the light-emitting source and the light-irradiating unit with an optical fiber.

BRIEF DESCRIPTION OF THE DRAWINGS

FIG. 4 is a block diagram showing a specific example of a first corrective value calculating unit in the block diagram of FIG. 2;

BEST MODE FOR CARRYING OUT THE INVENTION

The best for carrying out the invention will now be described in detail with reference to the accompanying drawings.

Figure 1:
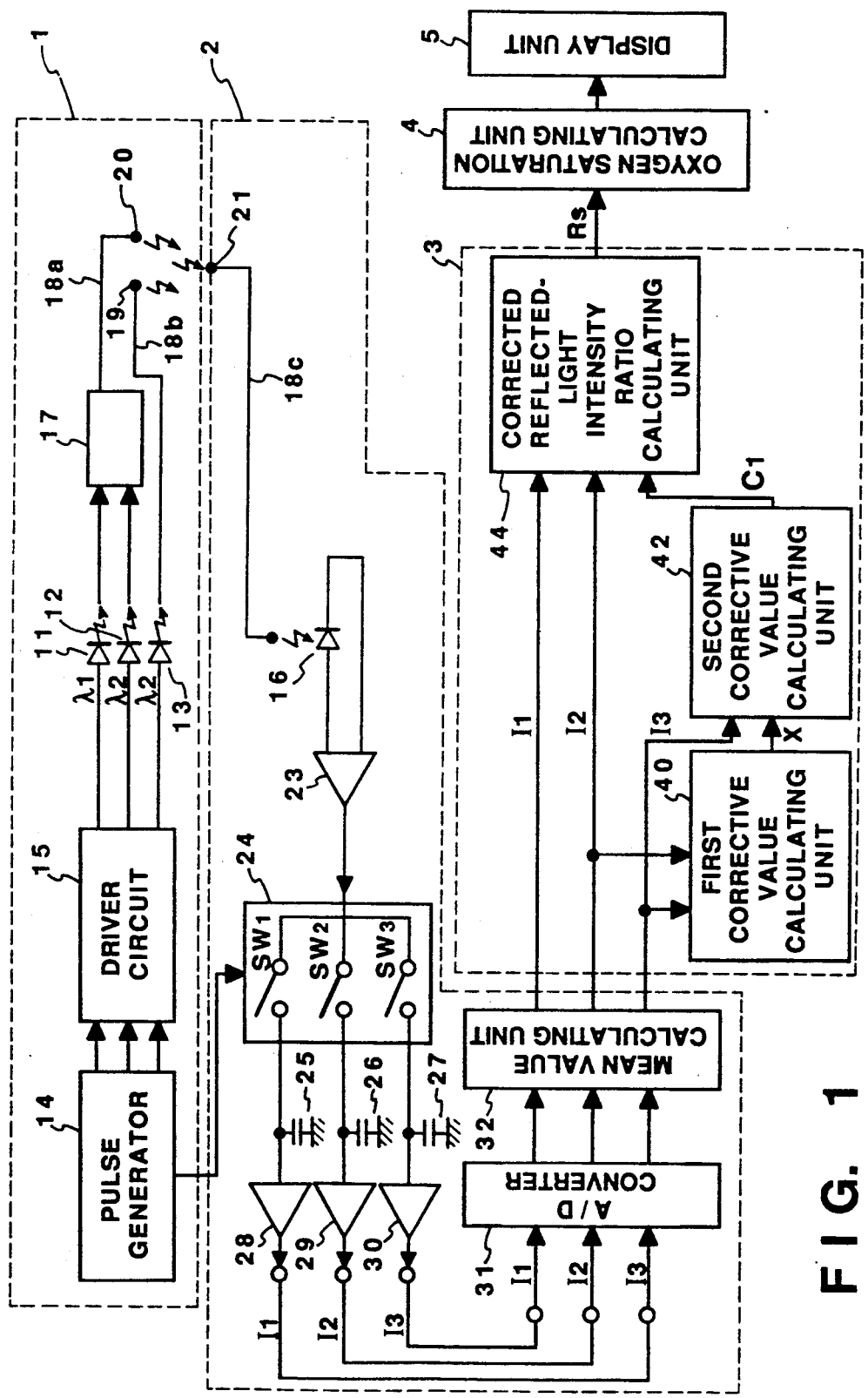
FIG. 1 is a block diagram of a first embodiment of an apparatus for measuring degree of oxygen saturation according to the present invention.

As shown in FIG. 1, an apparatus for measuring the degree of oxygen saturation of hemoglobin includes a light-irradiating circuit 1, a detecting unit 2 for detecting the intensity of light reflected from blood irradiated with light from the light-irradiating circuit 1, a correcting unit 3 which corrects for the influence of hematocrit value, a unit 4 for calculating the degree of oxygen saturation using the output of the correcting unit 3, and a display unit 5 for displaying the output of the oxygen saturation calculating unit 3.

The light-irradiating circuit 1 has a first light-irradiating unit for irradiating the blood with light of a first wavelength, a second light-irradiating unit for irradiating the sample with light of a second wavelength different from the light of the first wavelength, and third light-irradiating means for irradiating the blood with light of the second wavelength.

In the arrangement shown in FIG. 1, the first light-irradiating unit and the second light-irradiating unit are constituted by a first light-emitting source for emitting light of the first wavelength, a second light-emitting source for emitting light of the second wavelength, a common light-irradiating unit for irradiating the blood with the light from the first light-emitting source and second light-emitting source, and a third light-irradiating unit for irradiating the blood with light of the second wavelength.

More specifically, the light-irradiating circuit 1 comprises a light-emitting source and a light-irradiating unit for irradiating the blood with light from the light-emitting source. The light-emitting source comprises three light-emitting diodes 11, 12, 13. The light-emitting diode 11 emits light having a wavelength of about 660 nm ($\lambda_1$), and the light-emitting diodes 12, 13 each emit light having a wavelength of about 800 nm ($\lambda_2$). The light emitting diodes 11, 12, 13 are arranged so as to emit light alternately by being driven through a driver circuit 15 to which pulses of a predetermined interval and pulse width are applied by a pulse generator 14 so as not to overlap in time. The light emitted by the light-emitting diode 11 and the light emitted by the light-emitting diode 12 passes through a photocoupler 17 and a light-emitting optical fiber 18a to irradiate the blood from a light-irradiating portion 20 formed by the end face of the optical fiber 18a. By adopting such an arrangement, a single light-irradiating portion 20 suffices and the apparatus can be made small in size. In addition, the irradiating portion for light of wavelength $\lambda_1$ from the light-emitting diode 11 and the irradiating portion for light of wavelength $\lambda_2$ from the light-emitting diode 12 can be placed at the same distance from the detecting unit, described below.

The light emitting by the light-emitting diode 13 passes through a light-emitting optical fiber 18b to irradiate the blood from a light-irradiating portion 19 formed by the end face of the optical fiber 18b.

The invention is not limited to the arrangement shown in FIG. 1, for it is permissible to adopt an arrangement in which the light-irradiating circuit 1 is composed of three light-emitting sources and three light-irradiating portions for irradiating the blood with the light from respective ones of the light-emitting sources, or in which the light-irradiating circuit 1 is constituted by a light-emitting source for emitting the light of the first wavelength, a light-irradiating portion for irradiating the blood with the light from this light-emitting portion, a shared light-emitting source for emitting light of the second wavelength, and two light-irradiating portions for irradiating the blood, from different positions, with light from this light-emitting source.

The detecting unit 2 is for detecting the intensity of the light, which is emitted by the light-irradiating circuit 1, after the light is reflected from the blood. In the arrangement shown in FIG. 1, a photodetecting portion 21 of the detecting unit 2 is formed by the end face of a light-receiving optical fiber 18c and is so provided that the distance from the light-irradiating portion 19 differs from the distance from the light-irradiating portion 20.

Figure 2:
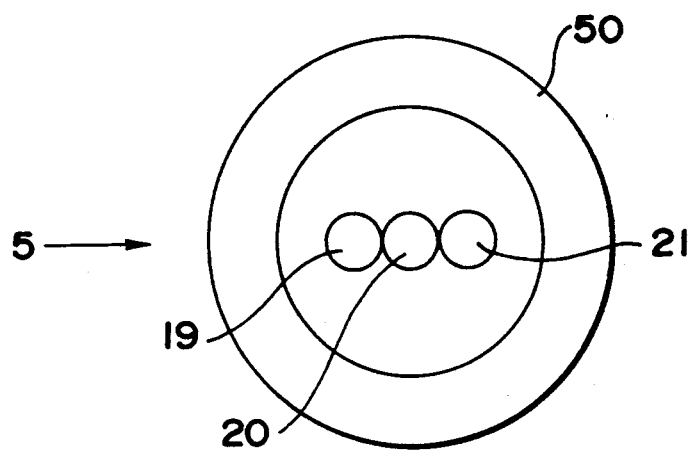
FIG. 2 is an end view showing an example of a sensor probe used in the embodiment of the apparatus for measuring degree of oxygen saturation.

FIG. 2 illustrates a specific example of the end face of a sensor probe 50 having the light-irradiating portions 19, 20 of the light-irradiating circuit 1 and the photodetecting portion 21 of the light detecting unit.

Two light-emitting optical fibers and one light-receiving fiber are linearly arrayed. The center-to-center distance between the light-irradiating portion 20 formed by the end face of the light-emitting optical fiber and the photodetecting portion 21 formed by the end face of the light-receiving optical fiber is 0.26 mm, and the center-to-center distance between the light-irradiating portion 19 formed by the end face of the light-emitting optical fiber and the photodetecting portion 21 formed by the end face of the light-receiving optical fiber is 0.50 mm. Thus, the optical fibers are provided so that these distances differ from each other. The fibers are fixed by an epoxy resin type bonding agent. Multicomponent glass with a core diameter of 200 μm was used as the optical fiber. The peripheral portion of the end face of the sensor probe 50 is smoothly polished so as not to lose its light transmissivity and in order to prevent clotting of blood. Though the above-described sensor probe has the single photodetecting portion 21 in order to make the sensor probe small in size, the invention is not limited to this arrangement and a plurality of the photodetecting portions 21 can be provided.

Figure 3:
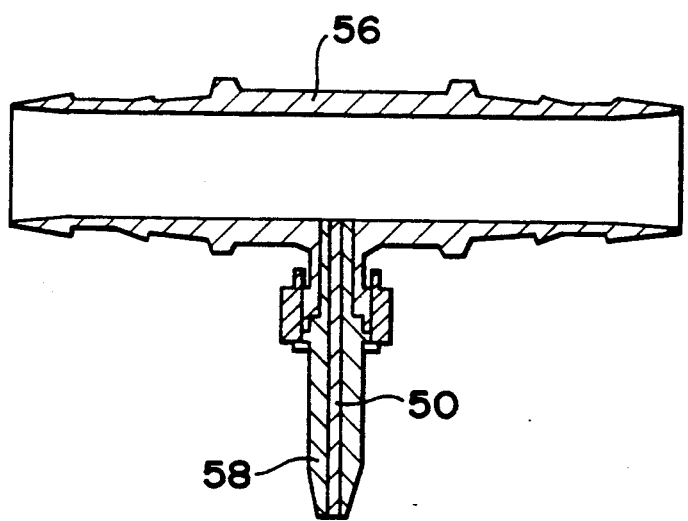
FIG. 3 is a sectional view of a connector to which the sensor probe shown in FIG. 2 is attached.

FIG. 3 illustrates a state in which the sensor probe 50 is attached to a connector 56 capable of being mounted in an extracorporeal circulating circuit (not shown) of an artificial lung, by way of example. The connector 56 has port 58, which is for attaching the sensor probe 50, projecting outwardly from a point midway along the axial length of the connector. The end face of the sensor probe 50 is worked so that the inner wall surface of the connector 56 and the end face of the sensor probe 50 will be substantially flush when the probe is attached to the connector 56. This is so that the blood flowing through the connector 56 will not be disturbed.

The detecting unit 2 has a photodiode 16 and a detecting amplifier 23 which receive the light detected by the photodetecting portion 21 and transmitted by the light-receiving optical fiber 18c. The photodiode 16 generates a current conforming to the intensity of the light signal. This current is converted into a voltage signal by the detecting amplifier 23. The detecting unit 2 has a signal separating circuit for separating the voltage signal from the detecting amplifier 23 into signals corresponding to the light-emission wavelengths of the light-emitting diodes 11, 12, 13. The signal separating circuit is constituted by an analog switch 24, capacitors 25, 26, 27 and buffer amplifiers 28, 29, 30.

The analog switch 24 has three switches SW1, SW2, SW3 turned "ON and "OFF" by a signal from the pulse generator 14. For example, when the light emitting diode 11 emits light, the signal from the pulse generator 14 is applied to the analog switch 24 so that only SW1 assumes the "ON" state. As a result, the voltage signal from the detecting amplifier 23 is applied to the capacitor 25 to produce a mean signal voltage across the ends of the capacitor 25. This indicates the intensity of the reflected light of wavelength $\lambda_1$, in which the light is emitted by the light-emitting diode 11, irradiates the blood from the light-irradiating portion 20, is reflected from the blood and then received by the photodiode 16 via the photodetecting portion 21. The mean signal voltage is continuously outputted through the buffer amplifier 28 to form a signal $I_1$ indicative of reflected-light intensity. Similarly, a like operation is performed by a combination of the light-emitting diode 12, SW2 of the analog switch 24, capacitor 26 and buffer amplifier 29, whereby a signal $I_2$ indicative of the reflected-light intensity of wavelength $\lambda_2$ from light-emitting diode 12 is outputted. Further, a like operation is performed by a combination of the light-emitting diode 13, SW3 of the analog switch 24, capacitor 27 and buffer amplifier 30, whereby a signal $I_3$ indicative of the reflected-light intensity of wavelength $\lambda_2$ from light-emitting diode 13 is outputted.

Further, the detecting unit 2 has a processor for the reflected-light intensity signals $I_1$, $I_2$, $I_3$ outputted by the signal separating circuit. The signal processor has an analog-digital converter 31 for converting the reflected-light intensity signals $I_1$, $I_2$, $I_3$ into digital signals, and a mean value calculating unit 32 for computing mean values upon storing the digitized reflected-light intensity signals $I_1$, $I_2$, $I_3$ outputted by the analog-digital converter 31 a predetermined number (n) of times or within a predetermined period of time. The correcting unit 3 which corrects for the influence of the hematocrit value has a first corrective value calculating unit 40, a second corrective value calculating unit 42 and a calculating unit 44 for calculating a corrected reflected-light intensity ratio.

The first corrective value calculating unit 40 has an arithmetic unit for computing a reflected-light intensity ratio ($I_2/I_3$) from one digitized reflected-light intensity signal $I_2$ and one digitized reflected-light intensity signal $I_3$ (e.g., digitized signals of the reflected-light intensity signals $I_2$, $I_3$ at the start of measurement) outputted by the mean value calculating unit 32. The output of the unit for computing the reflected-light intensity ratio ($I_2/I_3$) is delivered as a first corrective value. In this case, therefore, the first corrective value calculating unit 40 is one which computes the reflected-light intensity ratio ($I_2/I_3$) from the digitized reflected-light intensity signals $I_2$, $I_3$. The first corrective value is a fixed corrective value until a new first corrective value is computed.

The construction of the first corrective value calculating unit 40 shown in FIG. 4 will now be described. Numeral 60 denotes a unit for computing the reflected-light intensity ratio ($I_2/I_3$), 62 a measurement value input unit for inputting a measurement value obtained by sampling blood and measuring the hemoglobin concentration of the blood, and 63 an Hb calibration curve recorder for storing the following reference correlation function h(x):

$$h(x) = b_2 \cdot x^2 + b_1 \cdot x + b_0$$

[where $x = I_2/I_3$, and h(x) is referred to as an Hb calibration curve hereinafter). This function is a higher-order correlation curve (e.g., a second-degree regression curve) calculated from $I_2/I_3$, which is obtained from several kinds of blood, regarding animal species, the same as the blood which has already undergone measurement, and from the hemoglobin concentration Hb. Numeral 64 denotes an inverse function g(Hb) memory for storing the inverse function g(Hb) of h(x). Numeral 65 designates an arithmetic unit which uses the inverse function g(Hb) to calculate a reflected-light intensity ratio $[I_2/I_3]_s$ corresponding to the hemoglobin concentration inputted by the measurement value input unit 62. Numeral 66 represents an arithmetic unit for calculating $$(I_2/I_3)/[I_2/I_3]_s (=A)$$

from $[I_2/I_3]_s$, which is outputted by the arithmetic unit 65, and ($I_2/I_3$), which is outputted by the arithmetic unit 60 that computes the reflected-light intensity ratio ($I_2/I_3$) from the single digitized reflected-light intensity signal $I_2$ and single reflected-light intensity signal $I_3$ outputted by the mean value calculating unit 32. Numeral 67 represents a hemoglobin concentration reference value (Hb') input unit for inputting a reference value of hemoglobin concentration. Numeral 68 denotes an arithmetic unit for calculating a reflected-light intensity ratio function g(Hb') from the Hb calibration curve outputted by the Hb calibration curve memory 63 and the hemoglobin concentration reference value (Hb') (e.g., a hemoglobin concentration of 15%). Numeral 69 denotes an arithmetic unit for calculating the first corrective value $$X = [I_2/I_3]_{Hb=Hb'} = A \times g(Hb')$$

from A outputted by the arithmetic unit 66 and the reflected-light intensity ratio function g(Hb'), which is obtained from the reflected-light intensity ratio g(Hb') arithmetic unit 68. In this case also the first corrective value is a fixed corrective value until a new first corrective value is calculated.

The foregoing description relates to a case in which the apparatus is provided with the Hb calibration curve memory 63, hemoglobin concentration reference value (Hb') input unit 67 and the arithmetic unit 68 for calculating the reflected-light intensity ratio g(Hb') from the hemoglobin concentration reference value (Hb') (e.g., a hemoglobin concentration of 15%) obtained from the Hb calibration curve of the Hb calibration curve memory 63. However, the Hb calibration curve memory 63, hemoglobin concentration reference value (Hb') input unit 67 and the arithmetic unit 68 for calculating the reflected-light intensity ratio g(Hb') can be deleted by fixing the hemoglobin concentration reference value (Hb') at, e.g., a hemoglobin concentration of 15% beforehand, and replacing these units with a memory which stores the value of reflected-light intensity g(Hb') calculated from the Hb calibration curve prevailing at this time (i.e., when the hemoglobin concentration is 15%).

The first corrective value signal X ($=[I_2/I_3]_{Hb=Hb'}$) outputted by the first corrective value calculating unit 40 enters the second corrective value calculating unit 42 along with the digitized reflected-light intensity signal $[I_3]$ outputted continuously by the mean value calculating unit 32. The second corrective value calculating unit 42 calculates a second corrective value $C_1$, based on the following equation, using a previously stored constant $C_0$:

$$C_1 = C_0 \times [I_3] \times [I_2/I_3]_{Hb=Hb'}$$

The second corrective value signal $C_1$ outputted by the second corrective value calculating unit 42 enters the corrected reflected-light intensity ratio calculating unit 44 along with the digitized reflected-light intensity signals $[I_1]$, $[I_2]$ outputted continuously by the mean value calculating unit 32. The calculating unit 44 computes a corrected reflected-light intensity ratio $R_s$ from each of the foregoing signals in accordance with the following equation:

$$R_s = ([I_1] - C_1)/([I_2] - C_1)$$

The oxygen saturation calculating unit 4 stores a reference correlation function f(x), $x = R_s$ $$f(x) = a_3 \cdot R_s^3 + a_2 \cdot R_s^2 + a_1 \cdot R_s + a_0 \ (=SO_2)$$

obtained by a third order regression of a correlation curve between the corrected reflected-light intensity ratio $R_s$ ($=([I_1]-C_1)/([I_2]-C_1)$) of data from several types of blood measured in advance, and the degree of oxygen saturation at this time. The calculating unit 4 computes the degree $SO_2$ of oxygen saturation from the corrected reflected-light intensity ratio $R_s$ outputted by the corrected reflected-light intensity ratio calculating unit 44. The constant $C_0$ of the second corrected value $C_1$ indicates the variance in the data regarding the reference correlation function f(x) in the form of a standard deviation and is decided in such a manner that this value is minimized.

The signal outputted by the oxygen saturation calculating unit 4 is displayed by the display unit 5. It will suffice if the latter is means capable of providing an external indication of the measured value. Well-known means can be used, such as a cathode-ray tube, printer, liquid-crystal display unit or recorder.

Figure 5:
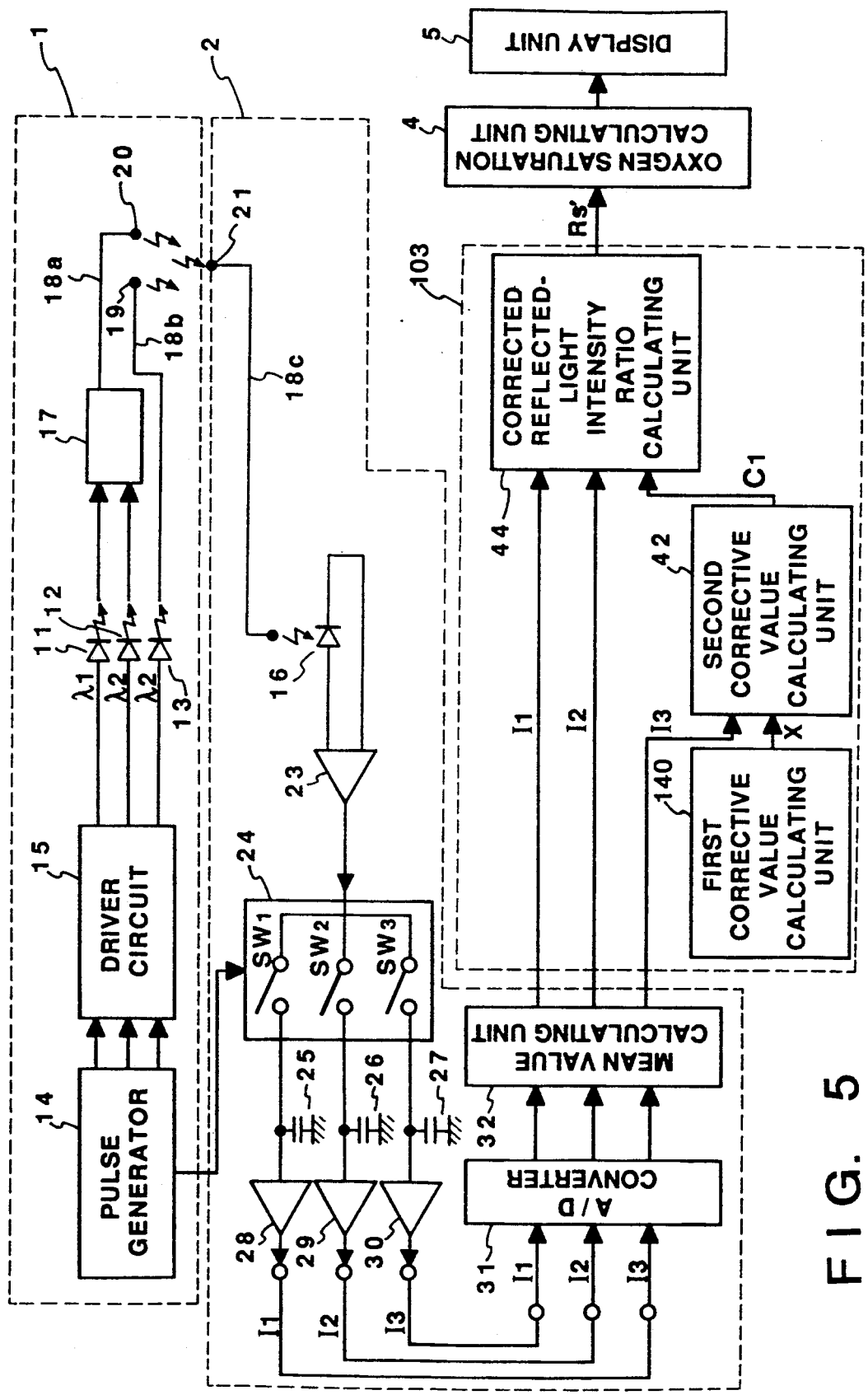
FIG. 5 is a block diagram of a second embodiment of an apparatus for measuring degree of oxygen saturation according to the present invention.

A second embodiment of the present invention will now be described using FIG. 5.

An apparatus for measuring the degree of oxygen saturation in this embodiment includes the light-irradiating circuit 1, the detecting unit 2 for detecting the intensity of light reflected from blood irradiated with light from the light-irradiating circuit 1, a correcting unit 103, the unit 4 for calculating the degree of oxygen saturation using the output of the correcting unit 103, and the display unit 5 for displaying the output of the oxygen saturation calculating unit 4.

The light-irradiating circuit 1, detecting unit 2, oxygen saturation calculating unit 4 and display unit 5 are the same as those shown in FIGS. 1 through 3. The correcting unit 103, which differs from the foregoing correcting unit, will now be described.

The correcting unit 103 has a first corrective value calculating unit 140, the second corrective value calculating unit 42 and the calculating unit 44 for computing a corrected reflected-light intensity ratio. The calculating unit 140 has a construction different from that shown in FIG. 1.

Figure 6:
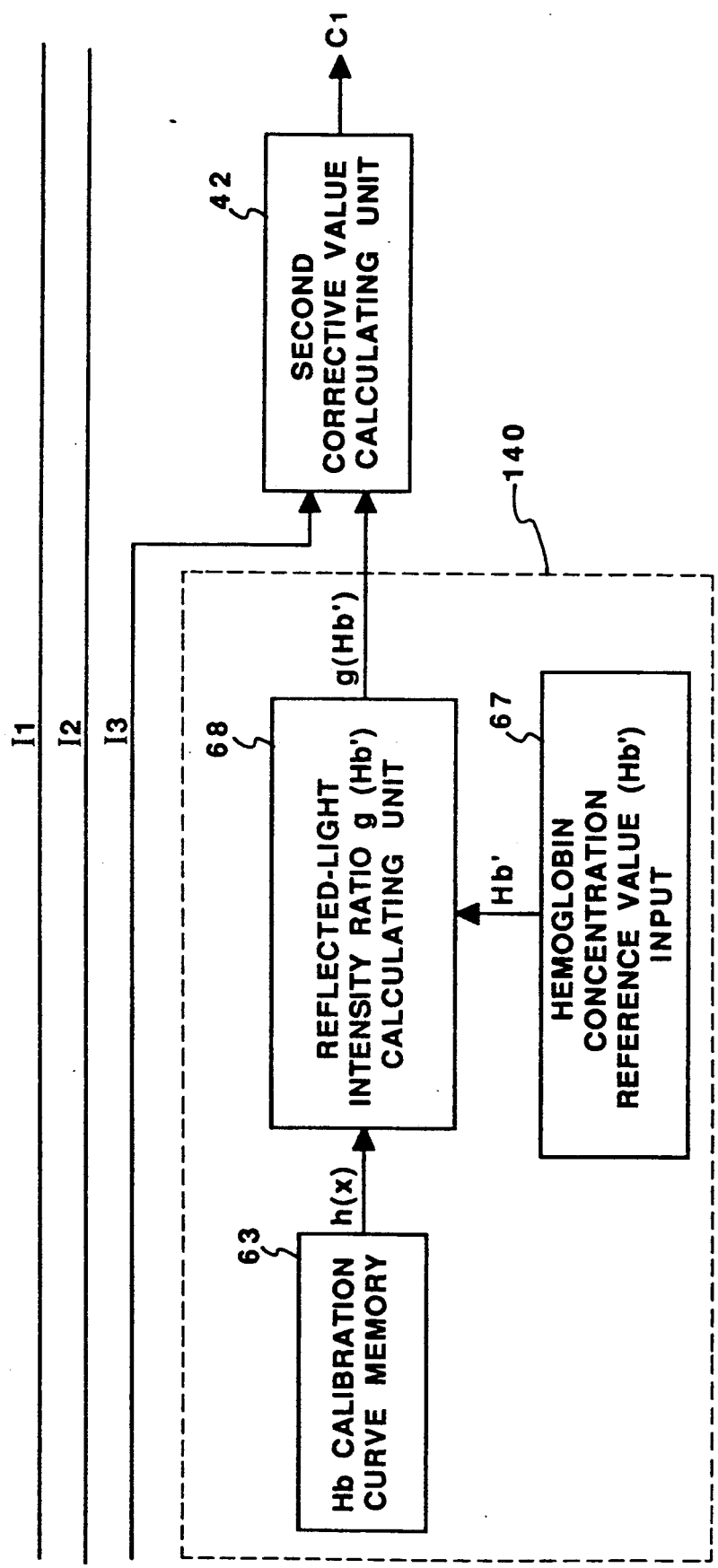
FIG. 6 is a block diagram showing a specific example of a first corrective value calculating unit in the block diagram of FIG. 4.

As shown in FIG. 6, the first corrective value calculating unit 140 comprises the Hb calibration curve memory 63 which stores the following reference correlation function h(x):

$$h(x) = b_2 \cdot x^2 + b_1 \cdot x + b_0$$

[where $x = I_2/I_3$, and h(x) is referred to as an Hb calibration curve hereinafter], this function being a higher-order correlation curve (e.g., a second-order regression curve) calculated from $I_2/I_3$, which is obtained from several kinds of blood of animal species the same as the blood which has already undergone measurement, and from the hemoglobin concentration Hb, the hemoglobin concentration reference value (Hb') input unit 67, and the arithmetic unit 68 for calculating the reflected-light intensity ratio function g(Hb'), which serves as the first corrective value, based on the hemoglobin concentration reference value (Hb') (e.g., a hemoglobin concentration of 15%) in accordance with the Hb calibration curve (reference correlation function) outputted by the Hb calibration curve memory 63. The Hb calibration curve memory 63, hemoglobin concentration reference value input unit 67 and reflected-light intensity ratio calculating unit 68 are the same as those described with reference to the block diagram of FIG. 4. Though the first corrective value calculating unit 140 has been described with regard to a case in which the apparatus is provided with the Hb calibration curve memory 63, hemoglobin concentration reference value (Hb') input unit 67 and the arithmetic unit 68 for calculating the reflected-light intensity ratio function g(Hb'), the Hb calibration curve memory 63, hemoglobin concentration reference value input unit 67 and the arithmetic unit 68 can be deleted by fixing the hemoglobin concentration reference value (Hb') at, e.g., a hemoglobin concentration of 15% beforehand, and adopting a memory which stores the value of reflected-light intensity g(Hb') function calculated from the Hb calibration curve prevailing at this time (i.e., when the hemoglobin concentration is 15%), just as in the case of FIG. 1.

The reflected-light intensity ratio function g(Hb') ($=[I_2/I_3]_{Hb=Hb'}$) outputted by the calculating unit 68 which computes the reflected-light intensity ratio function g(Hb') of the first corrective value calculating unit 140 enters the second corrective value calculating unit 42 along with the digitized reflected-light intensity signal [$I_3$] outputted continuously by the mean value calculating unit 32. The second corrective value calculating unit 42 calculates a second corrective value $C_1$, based on the following equation, using a previously stored constant $C_0$:

$$C_1 = C_0 \times [I_3] \times [I_2/I_3]_{Hb=Hb'}$$

The second corrective value signal $C_1$ outputted by the second corrective value calculating unit 42 enters the corrected reflected-light intensity ratio calculating unit 44 along with the digitized reflected-light intensity signals [$I_1$], [$I_2$] outputted continuously by the mean value calculating unit 32. The calculating unit 44 computes a corrected reflected-light intensity ratio $R_s$ from each of the foregoing signals in accordance with the following equation:

$$R_s = ([I_1] - C_1)/([I_2] - C_1)$$

The oxygen saturation calculating unit 4 has a memory which stores a reference correlation function f(x), (x = $R_s$)

$$f(x) = a_3 \cdot R_s^3 + a_2 \cdot R_s^2 + a_1 \cdot R_s + a_0 \ (= SO_2)$$

obtained by a third-order regression of a correlation curve between $R_s$ ($=([I_1]-C_1)/([I_2]-C_1)$) regarding data from several types of blood measured in advance, and the degree of oxygen saturation at this time. The calculating unit 4 computes the degree $SO_2$ of oxygen saturation from the corrected reflected-light intensity ratio $R_s$ outputted by the corrected reflected-light intensity ratio calculating unit 44. The constant $C_0$ of the second corrected value $C_1$ indicates the variance in the data regarding the reference correlation function f(x) in the form of a standard deviation and is decided in such a manner that this value is minimized. The signal outputted by the calculating unit 4 is displayed by the display unit 5.

A method of measuring the degree of oxygen saturation by the oxygen saturation measuring apparatus of the present invention will now be described in accordance with an embodiment with reference to the flowcharts of FIGS. 7 through 9.

EMBODIMENT 1

Figure 7:
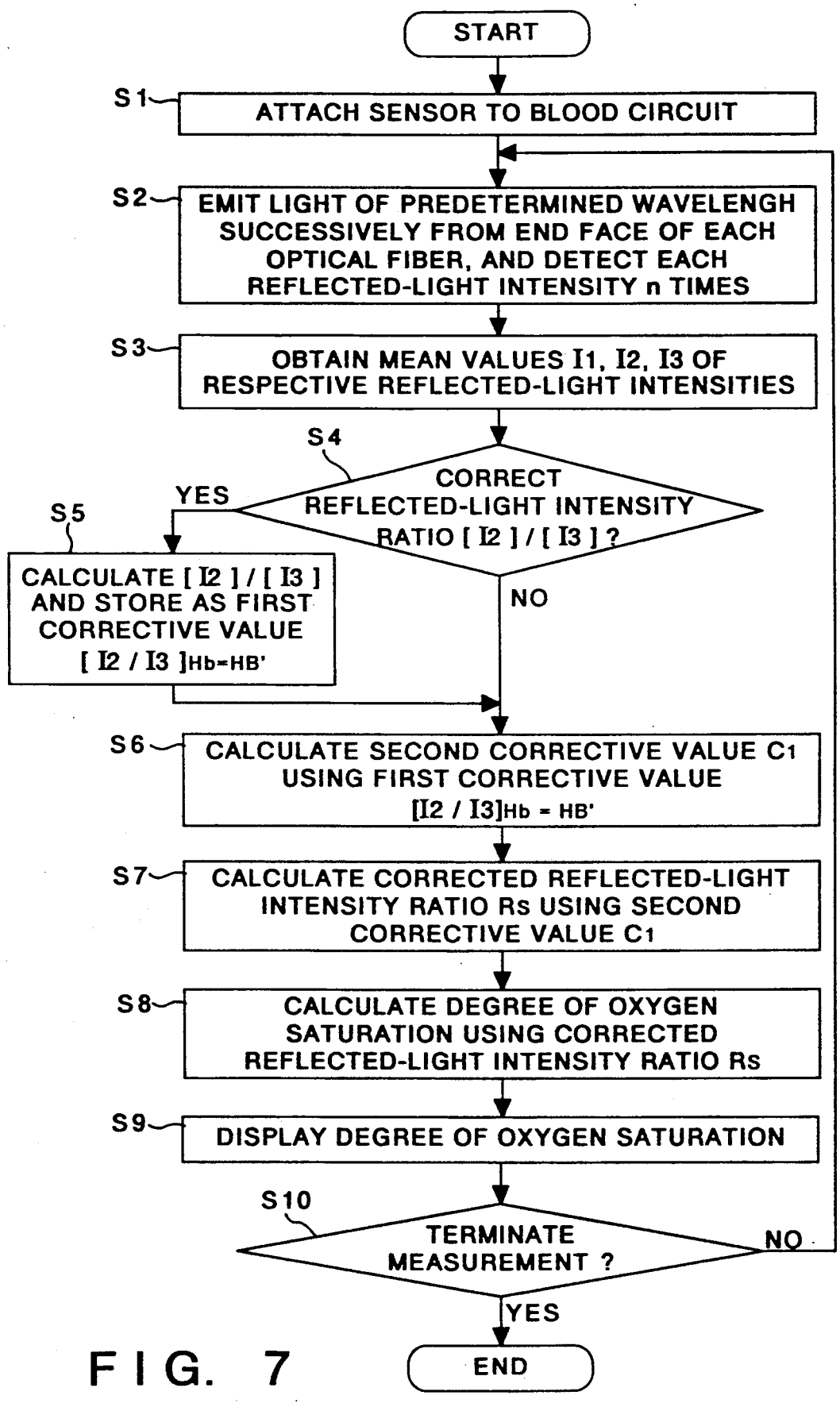
FIG. 7 is a flowchart showing a method of measuring degree of oxygen saturation by the apparatus for measuring degree of oxygen saturation according to the first embodiment.

In accordance with the embodiment shown in FIG. 7, a connector of the configuration shown in FIG. 3 to which the sensor probe of FIG. 2 has been mounted is attached to a blood circuit at a step S1. Next, at step S2, blood is successively irradiated with the light of the approximate wavelengths of 660 nm ($\lambda_1$) and 800 nm ($\lambda_2$) from the light-irradiating portion 20 formed by the end face of the optical fiber of the light-irradiating unit shown in FIG. 1, and with the light of the approximate wavelength of 800 nm from the light-irradiating portion 19 formed by the end face of the optical fiber. The intensity of light reflected from the blood irradiated with each light beam from the light-irradiating unit 1 is detected n times by the detecting unit 2. At step S3, the mean value of each reflected-light intensity detected n times is calculated and the digitized reflected-light intensity signals $I_1$, $I_2$, $I_3$ are outputted.

It is determined at step S4 whether to correct the reflected-light intensity ratio $I_2/I_3$ as a correction for preventing the influence of the hematocrit value. The program proceeds to step S5 if the correction is to be performed.

At step S5, the reflected-light intensity ratio ($I_2/I_3$) is calculated from one (the initially outputted) digitized reflected-light intensity signal $I_2/I_3$ outputted at step S3, and this is stored as the first corrective value $[I_2/I_3]_{Hb=Hb'}$.

The second corrective value $C_1$ is obtained at step S6 in accordance with the equation $$C_1 = C_0 \times [I_3] \times [I_2/I_3] \text{ or}$$

$$C_1 = C_0 \times [I_3] \times [I_2/I_3]_{Hb=Hb'}$$

from the first corrective value stored at step S5 or, when a correction is not made at step S4, the uncorrected reflected-light intensity ratio $I_2/I_3$, the digital reflected-light intensity signal [$I_3$] continuously outputted at step S3, and the previously stored $C_0$ (0.23 in this embodiment).

The corrected reflected-light intensity ratio $R_s$ is obtained at step S7 in accordance with the equation $$R_s = ([I_1] - C_1)/([I_2] - C_1)$$

from the second corrective value $C_1$ outputted at step S6 and the digitized reflected-light intensity signals [$I_1$], [$I_2$] continuously outputted at step S3. By using the corrected reflected-light intensity ratio $R_s$ outputted at step S7, the degree of oxygen saturation is calculated at step S8 from the reference correlation function f(x), (x = $R_s$)

$$f(x) = a_3 \cdot R_s^3 + a_2 \cdot R_s^2 + a_1 \cdot R_s + a_0 \ (= SO_2)$$

{f(x) = $-4.165 R_s^3 + 38.08 R_s^2 - 136.0 R_s + 180.0$ in this embodiment} obtained by a third-order regression of a correlation curve between the corrected reflected-light intensity ratio $R_s$ ($=([I_1]-C_1)/([I_2]-C_1)$) of data from several types of blood measured in advance, and the degree of oxygen saturation. The degree of oxygen saturation calculated at step S8 is displayed on the display unit 5 at step S9. It is determined at step S10 whether measurement is to be terminated. If measurement is not terminated, the program returns to step S2 and the measurement described above is repeated.

Figure 10:
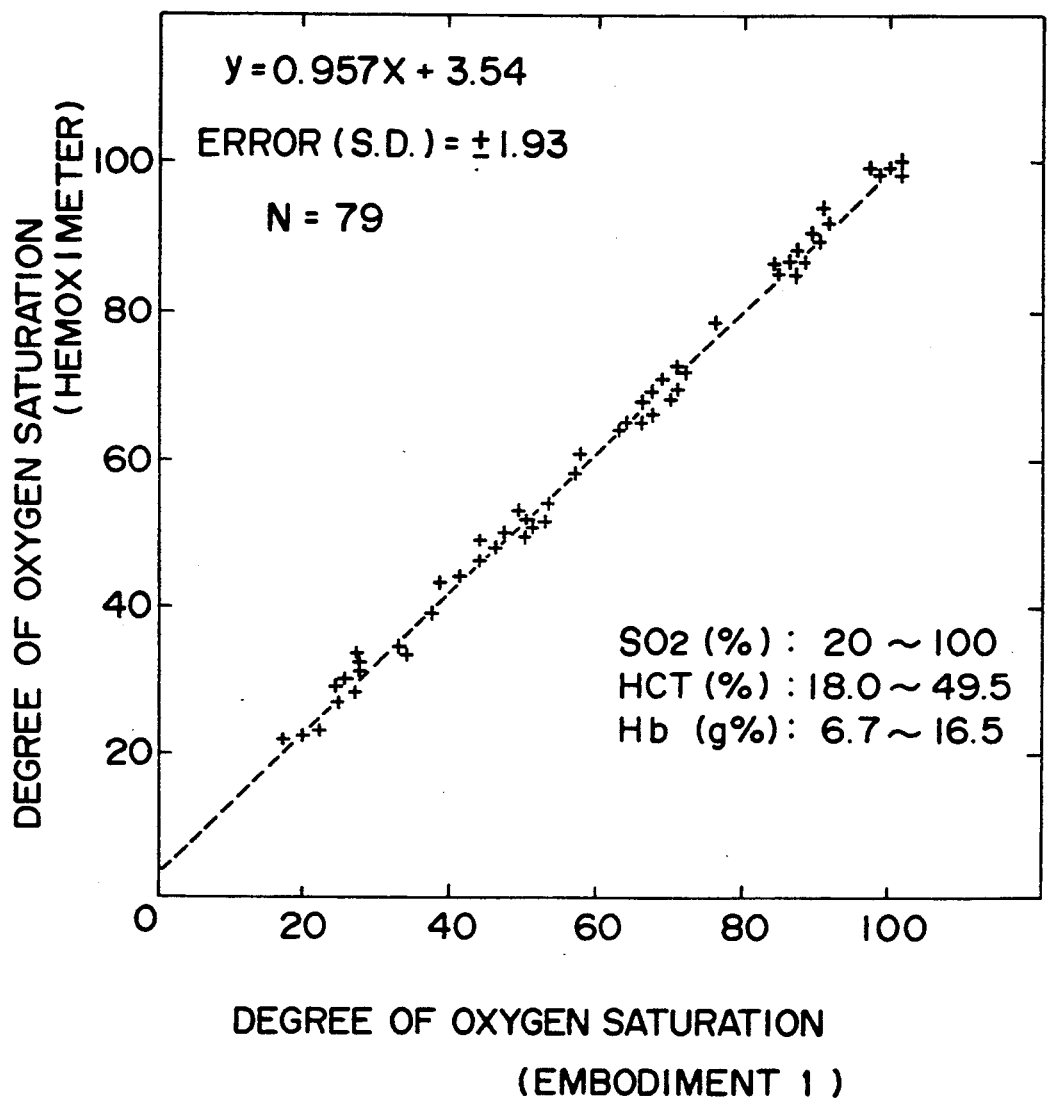
FIG. 10 is a view showing the relationship between degree of oxygen saturation obtained by the apparatus for measuring degree of oxygen saturation according to an embodiment and degree of oxygen saturation measured by an OSM2 hemoxymeter for purposes of contrast.

FIG. 10 shows the relationship between degree of oxygen saturation for a number (n = 79) of items of data using the method of embodiment 1 and degree of oxygen saturation measured with an OSM2 hemoxymeter (manufactured by Radiometer) used for purposes of contrast. It was found from these results that accurate measurement can be carried out, in which the value (x) of degree of oxygen saturation obtained in accordance with this embodiment approximates a correlation coefficient = 1 (y = x), with respect to the value (y) of degree of oxygen saturation obtained using the OSM2 hemoxymeter, with the error (S.D.) also being sufficiently small.

EMBODIMENT 2

Figure 8A:
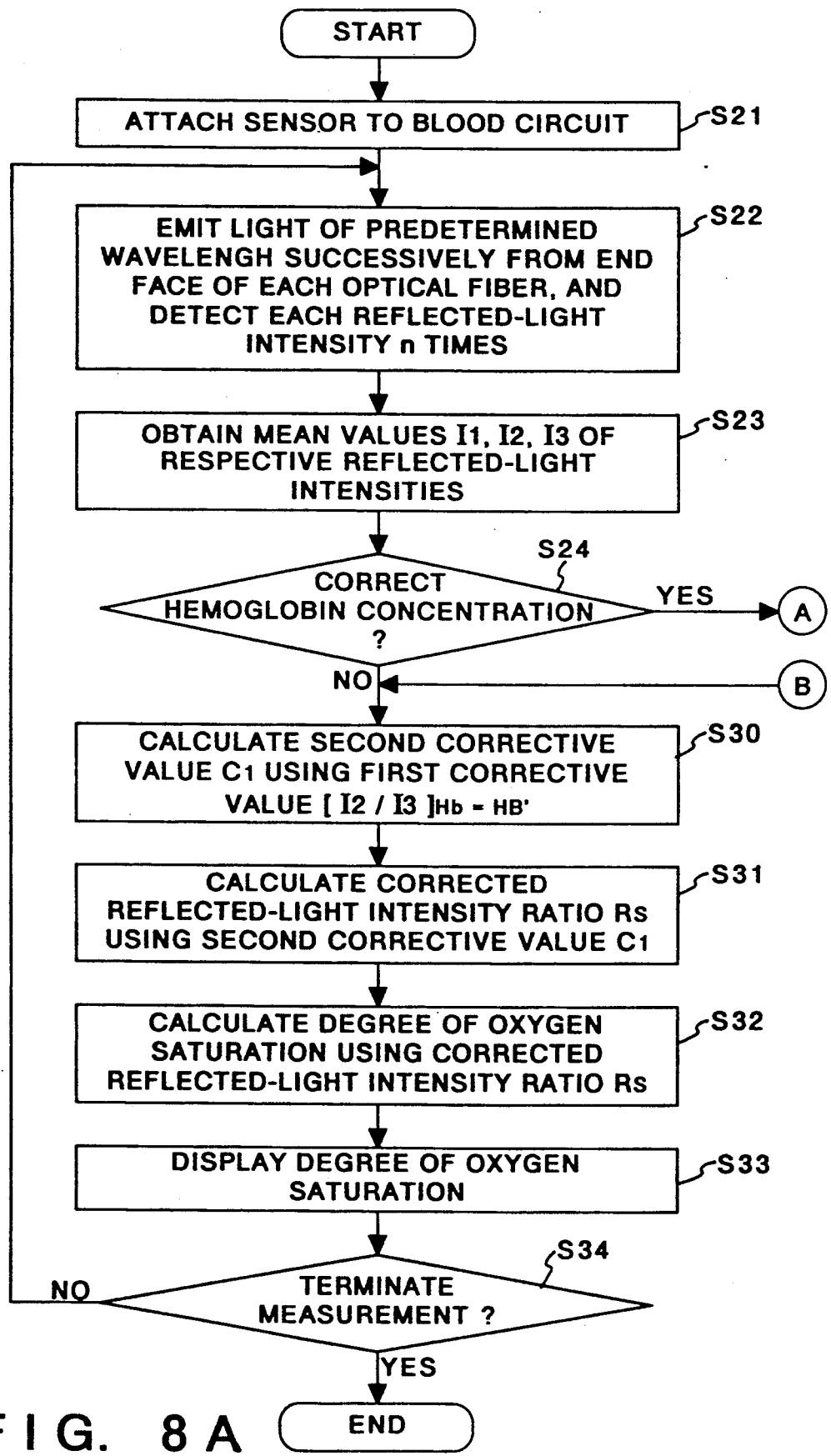
FIG. 8A and 8B are flowcharts showing a method of measuring degree of oxygen saturation by the apparatus for measuring degree of oxygen saturation according to the another embodiment.
Figure 8B:
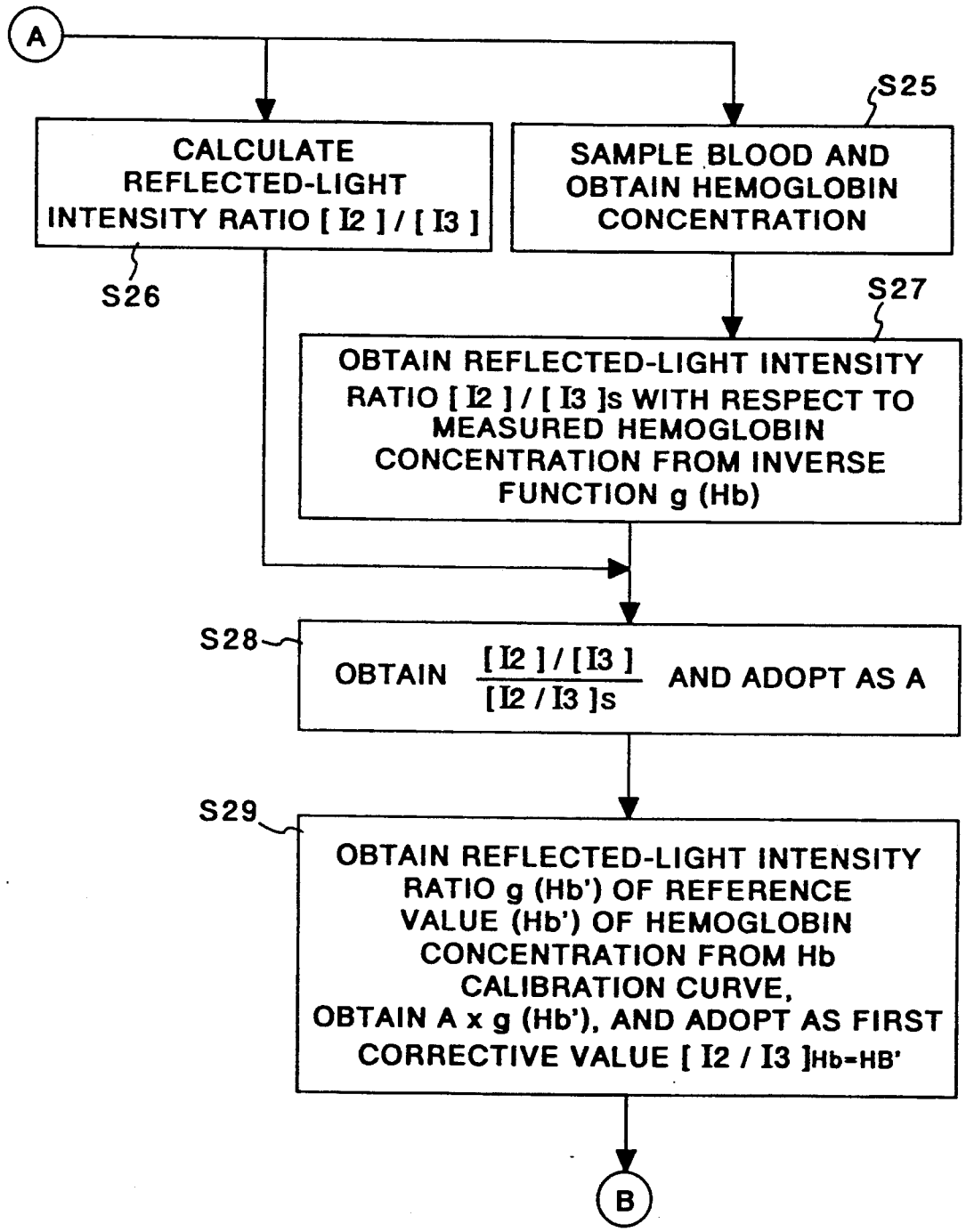

In accordance with embodiment 2 shown in FIG. 8, the mean value of each reflected-light intensity detected n times is calculated and the digitized reflected-light intensity signals $I_1$, $I_2$, $I_3$ are outputted at steps S21 through S23, just as at steps S1 through S3 of FIG. 7.

It is determined at step S24 whether to apply a correction to the hemoglobin concentration as a correction for preventing the influence of the hematocrit value. The program proceeds to step S25 or step S26 if the correction is to be performed. At step S26, the reflected-light intensity ratio ($I_2/I_3$) is calculated from one (the initially outputted) of each of the digitized reflected-light intensity signals $I_2$, $I_3$ outputted at step S23, whereby [$I_2/I_3$] is calculated.

At step S25, blood to be measured is sampled to measure hemoglobin concentration. The program then proceeds to step S27 to calculate the reflected-light intensity ratio [$I_2/I_3$]$_s$ corresponding to the measured hemoglobin concentration from the inverse function of the stored Hb calibration curve h(x), namely $$g(Hb) = 1.232 - \sqrt{1.151 - 0.04649 \times h(x)}$$

along with the reference correlation function h(x)

$$h(x) = b_2 \cdot x^2 + b_1 \cdot x + b_0$$

In this embodiment, $h(x) = -21.51x^2 + 53.02x - 7.912$.

[where $x = I_2/I_3$, and h(x) is referred to as an Hb calibration curve hereinafter). This function is a higher-order correlation curve (e.g., a second-order regression curve) calculated from $I_2/I_3$, which is obtained from several kinds of blood and already measured and stored, and from the hemoglobin concentration Hb.

Next, from [$I_2$]/[$I_3$] outputted at step S26 and [$I_2/I_3$]$_s$ outputted at step S27, the following ratio between these two is calculated at step S28:

$$([I_2]/[I_3])/[I_2/I_3]_s (=A)$$

The program then proceeds to step S29, at which the reflected-light intensity ratio g(Hb') of the hemoglobin concentration reference value (Hb') (a hemoglobin concentration of 15%) is calculated from the stored Hb calibration curve, and the first corrective value $$X = [I_2/I_3]_{Hb=Hb'} = A \times g(Hb')$$

is calculated from the foregoing and from A, which is outputted at step S28.

The second corrective value $C_1$ is obtained at step S30 in accordance with $$C_1 = C_0 \times [I_3] \times [I_2/I_3] \text{ or}$$

$$C_1 = C_0 \times [I_3] \times [I_2/I_3]_{Hb=Hb'}$$

from the first corrective value stored at step S29 or, when a correction is not made at step S24, the uncorrected reflected-light intensity ratio [$I_2/I_3$], the digital reflected-light intensity signal [$I_3$] continuously outputted at step S23, and the already stored constant $C_0$ (0.26 in this embodiment).

The corrected reflected-light intensity ratio $R_s$ is obtained at step S31 in accordance with the equation $$R_s = ([I_1] - C_1)/([I_2] - C_1)$$

from the second corrective value $C_1$ outputted at step S30 and the digitized reflected-light intensity signals [$I_1$], [$I_2$] continuously outputted at step S23.

By using the corrected reflected-light intensity ratio $R_s$ outputted at step S31, the degree of oxygen saturation is calculated at step S32 from the reference correlation function f(x), ($x = R_s$)

$$f(x) = a_3 \cdot R_s^3 + a_2 \cdot R_s^2 + a_1 \cdot R_s + a_0 (=SO_2)$$

{$f(x) = -4.165 R_s^3 + 38.08 R_s^2 - 136.0 R_s + 180.0$ in this embodiment} obtained by a third-order regression of a correlation curve between the corrected reflected-light intensity ratio $R_s$ $(= ([I_1] - C_1)/([I_2] - C_1))$ of data from several types of blood measured in advance, and the degree of oxygen saturation. The degree of oxygen saturation calculated at step S32 is displayed at step S33.

It is determined at step S34 whether measurement is to be terminated. If measurement is not terminated, the program returns to step S22 and the measurement described above is repeated.

Figure 11:
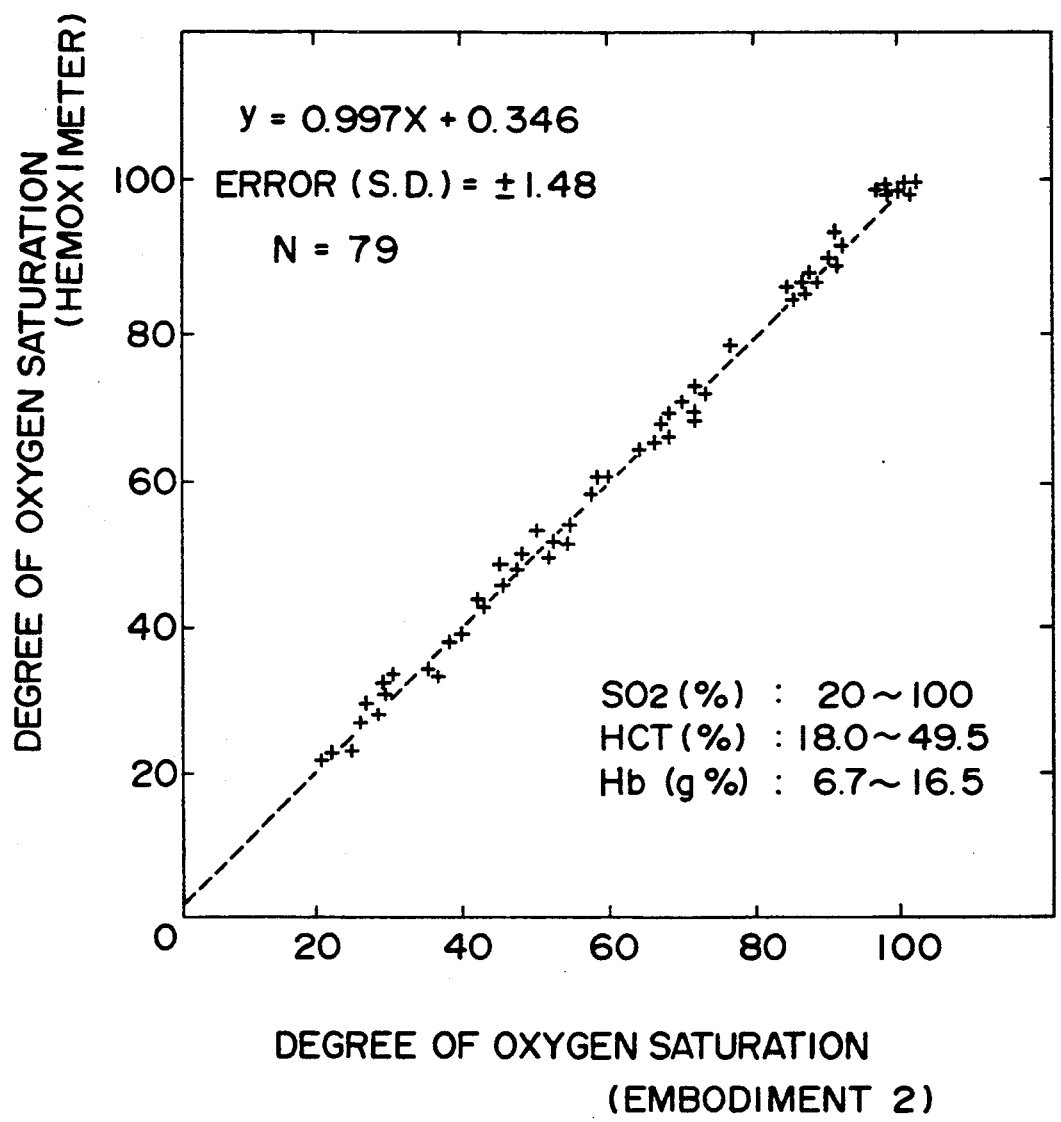
FIG. 11 is a view showing the relationship between degree of oxygen saturation obtained by the apparatus for measuring degree of oxygen saturation according to the first embodiment and degree of oxygen saturation measured by an OSM2 hemoxymeter for purposes of contrast.

FIG. 11 shows the relationship between degree of oxygen saturation obtained according to embodiment 2 and degree of oxygen saturation measured with an OSM2 hemoximeter (manufactured by Radiometer) used for purposes of contrast. It was found from these results that accurate measurement can be carried out, in which the value (x) of degree of oxygen saturation obtained in accordance with the method of this embodiment approximates a correlation coefficient = 1 (y = x), with respect to the value (y) of degree of oxygen saturation obtained using the OSM2 hemoximeter, with the error (S.D.) also being sufficiently small.

EMBODIMENT 3

Figure 9:
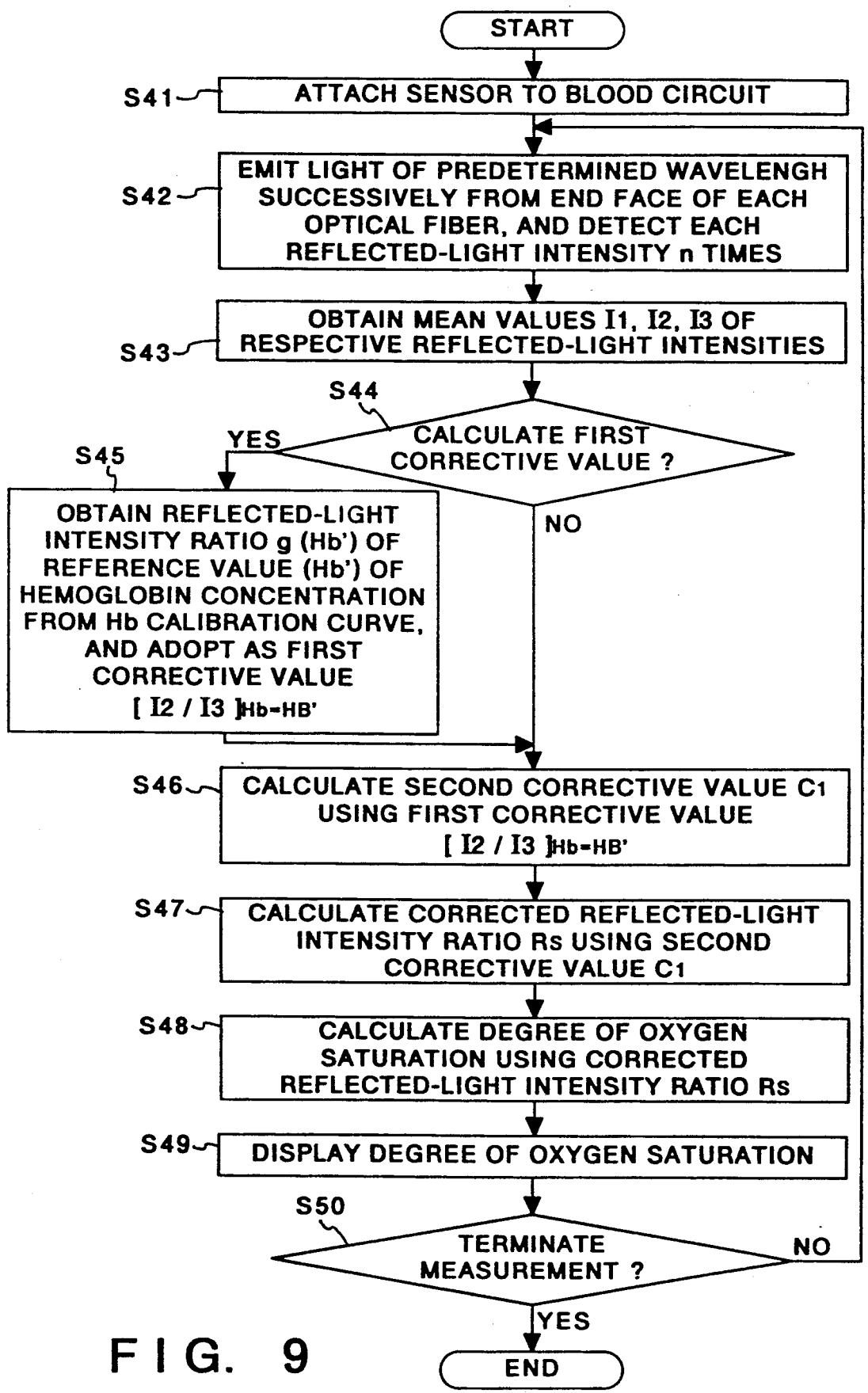
FIG. 9 is a flowchart showing a method of measuring degree of oxygen saturation by the apparatus for measuring degree of oxygen saturation according to the second embodiment.

In accordance with embodiment 3 shown in FIG. 9, the mean value of each reflected-light intensity detected n times is calculated and the digitized reflected-light intensity signals $I_1$, $I_2$, $I_3$ are outputted at steps S41 through S43, just as at steps S1 through S3 of FIG. 7. It is determined at step S44 whether to calculate the first corrective value. The program proceeds to step S45 if the correction is to be performed. At step S45, the reflected-light intensity ratio g(Hb') of the hemoglobin concentration reference value (Hb') (a hemoglobin concentration 15% in this embodiment) is calculated from the reference correlation function h(x)

$$h(x) = b_2 \cdot x^2 + b_1 \cdot x + b_0$$

which here is $h(x) = -69.60x^2 + 100.1x - 15.18$ [where $x = I_2/I_3$, and h(x) is referred to as an Hb calibration curve hereinafter), then the first corrective value [$I_1/I_2$]$_{Hb=Hb'}$ is calculated. This function is a higher-order correlation curve (e.g., a second-order regression curve) calculated from $I_2/I_3$, which is obtained from several kinds of blood and already measured and stored, and from the hemoglobin concentration Hb.

The second corrective value $C_1$ is obtained at step 46 in accordance with the equation $$C_1 = C_0 \times [I_3] \times [I_2/I_3] \text{ or}$$

$$C_1 = C_0 \times [I_3] \times [I_2/I_3]_{Hb=Hb'}$$

from the first corrective value stored at step S45 or, when a correction is not made at step S44, the uncorrected reflected-light intensity ratio [$I_2/I_3$], the digital reflected-light intensity signal [$I_3$] continuously outputted at step S43, and the previously stored $C_0$ (0.26 in this embodiment).

Next, the corrected reflected-light intensity ratio $R_s$ is obtained at step S47 in accordance with the equation $$R_s = ([I_1] - C_1)/([I_2] - C_1)$$

from the second corrective value $C_1$ outputted at step S46 and the digitized reflected-light intensity signals [$I_1$], [$I_2$] continuously outputted at step S43.

By using the corrected reflected-light intensity ratio $R_s$ outputted at step S47, the degree of oxygen saturation is calculated at step S48 from the reference correlation function $f(x)$, $(x = R_s)$ $$f(x) = a_3 \cdot R_s^3 + a_2 \cdot R_s^2 + a_1 \cdot R_s + a_0 \; (= SO_2)$$

{$f(x) = -4.165 R_s^3 + 38.08 R_s^2 - 136.0 R_s + 180.0$ in this embodiment} obtained by a third-order regression of a correlation curve between the corrected reflected-light intensity ratio $R_s$ ($= ([I_1] - C_1)/([I_2] - C_1)$) of data from several types of blood measured in advance, and the degree of oxygen saturation.

The degree of oxygen saturation calculated at step S48 is displayed on the display unit 5 at step S49. It is determined at step S50 whether measurement is to be terminated. If measurement is not terminated, the program returns to step S42 and the measurement described above is repeated.

Figure 12:
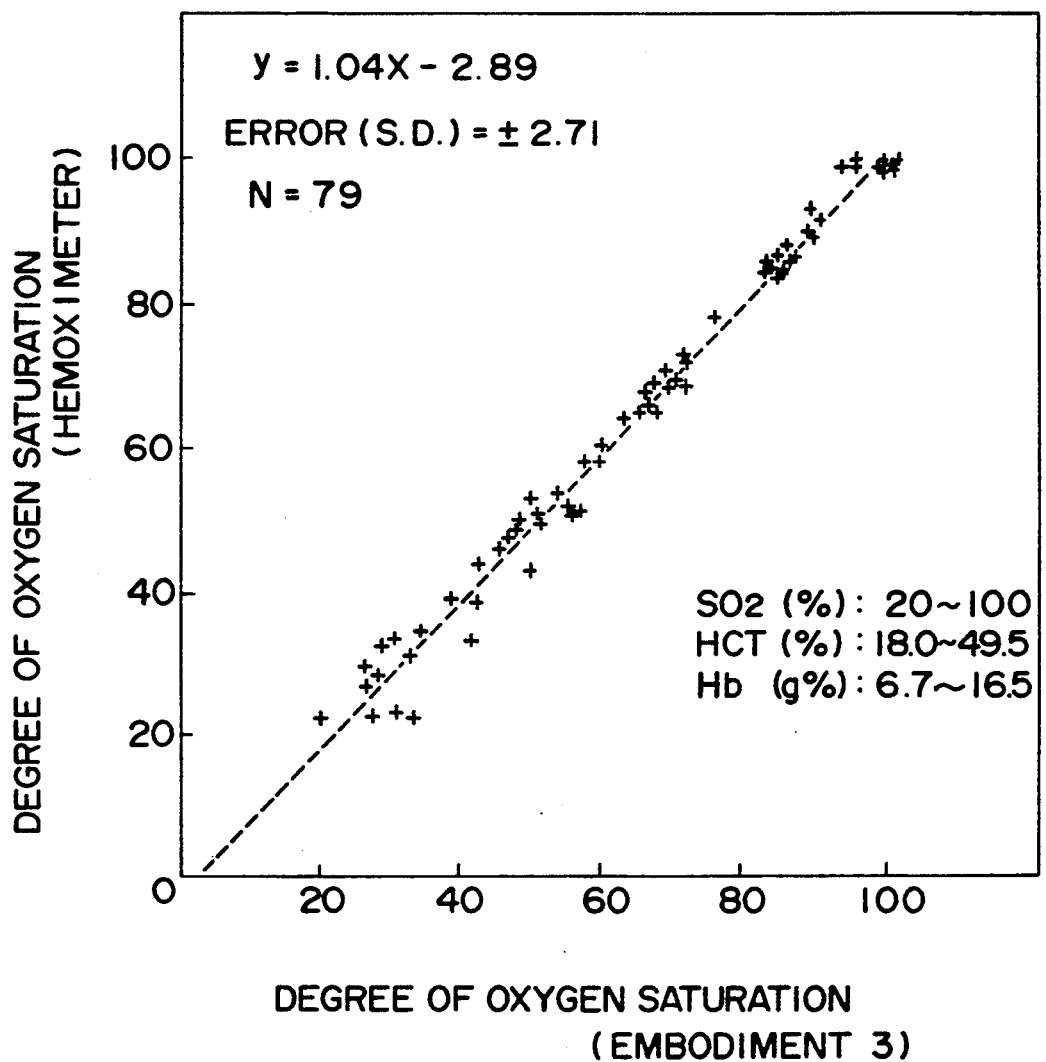
FIG. 12 is a view showing the relationship between degree of oxygen saturation obtained by the apparatus for measuring degree of oxygen saturation according to an embodiment of a second invention of the present application and degree of oxygen saturation measured by an OSM2 hemoxymeter for purposes of contrast.

FIG. 12 shows the relationship between degree of oxygen saturation obtained according to embodiment 3 and degree of oxygen saturation measured with an OSM2 hemoximeter (manufactured by Radiometer) used for purposes of contrast. It was found from these results that accurate measurement can be carried out, in which the value (x) of degree of oxygen saturation obtained in accordance with the method of this embodiment approximates a correlation coefficient = 1 (y = x), with respect to the value (y) of degree of oxygen saturation obtained using the OSM2 hemoximeter, with the error (S.D.) also being sufficiently small.

Measurement of hemoglobin concentration according to another embodiment of the present invention will now be described.

Figure 13:
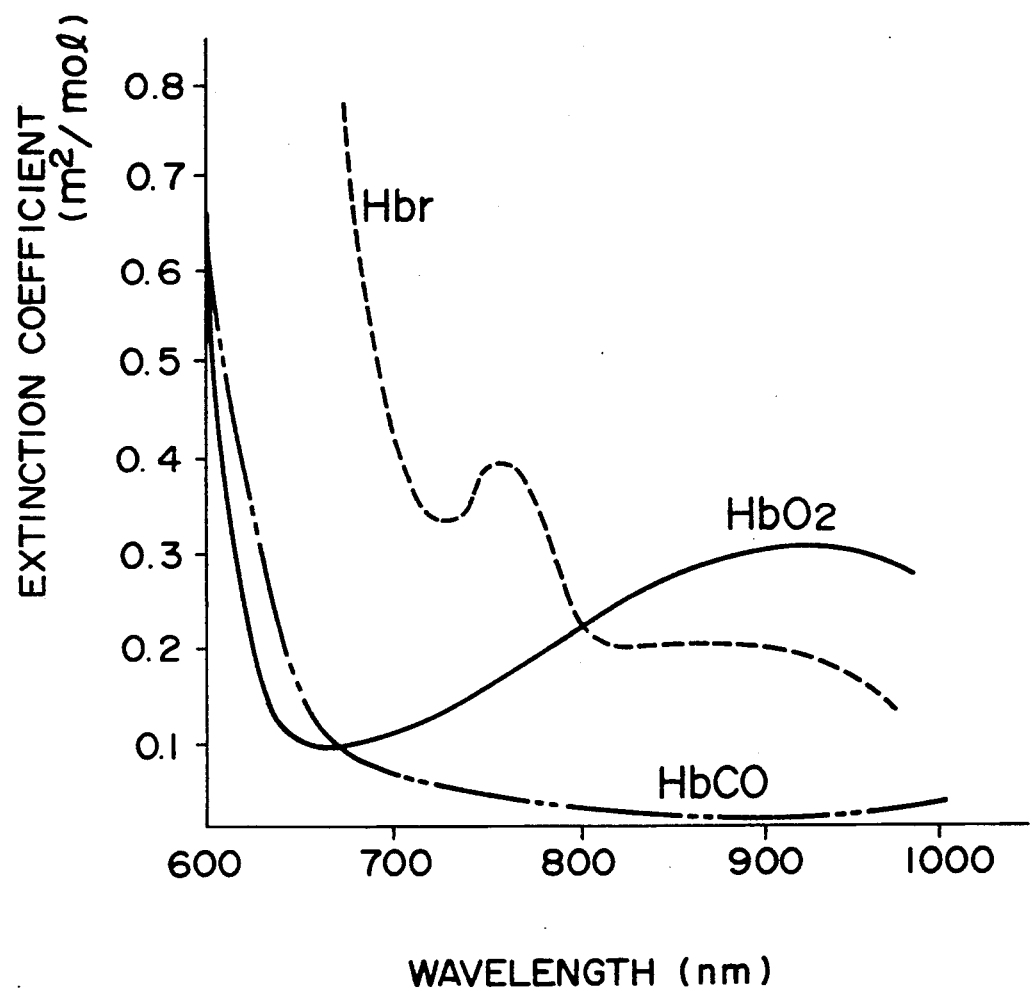
FIG. 13 is a view showing a common extinction characteristic of blood.
Figure 14A:
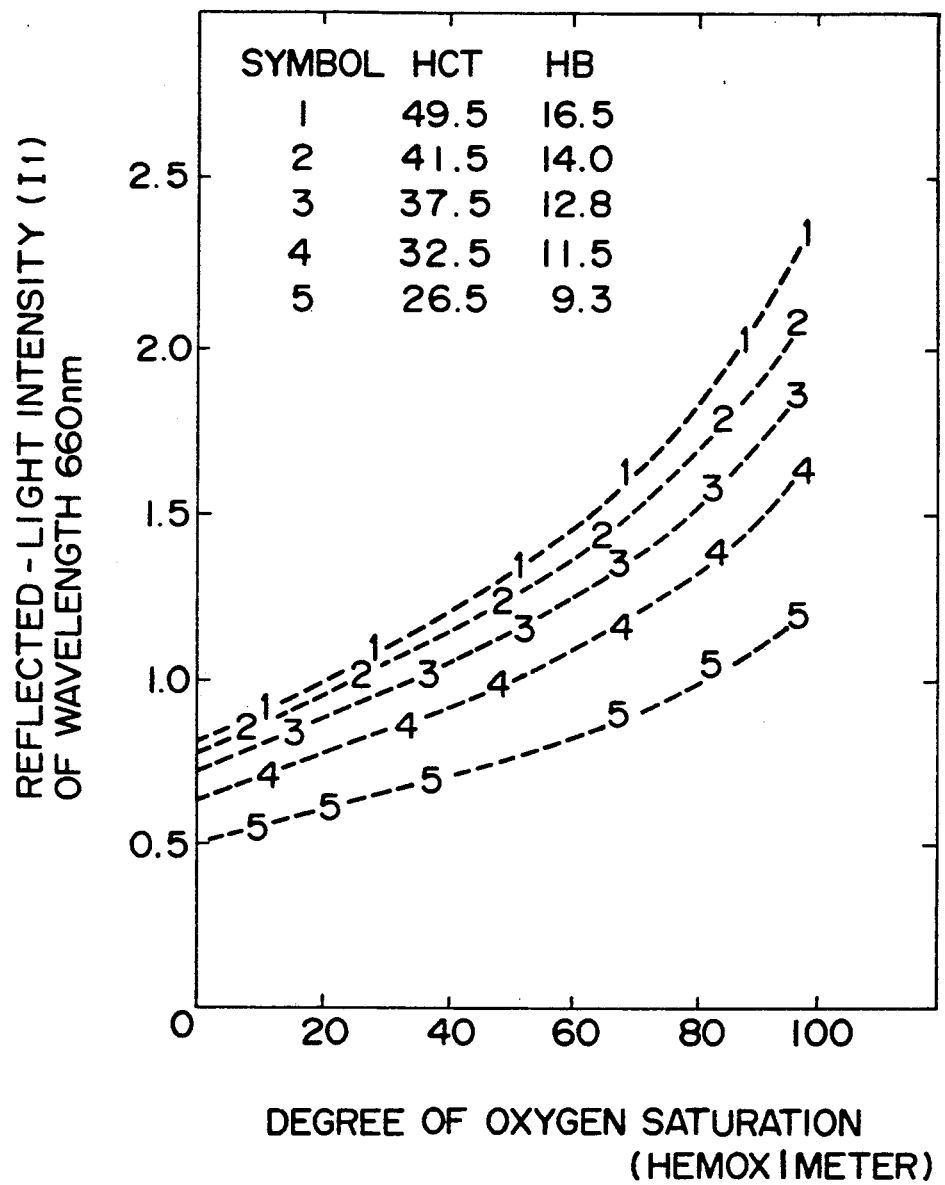
FIGS. 14A and 14B are diagrams in which the relationship between reflected light intensities at wavelengths of about 660 nm and about 800 nm, respectively, is plotted while varying the hematocrit value (HCT)
Figure 14B:
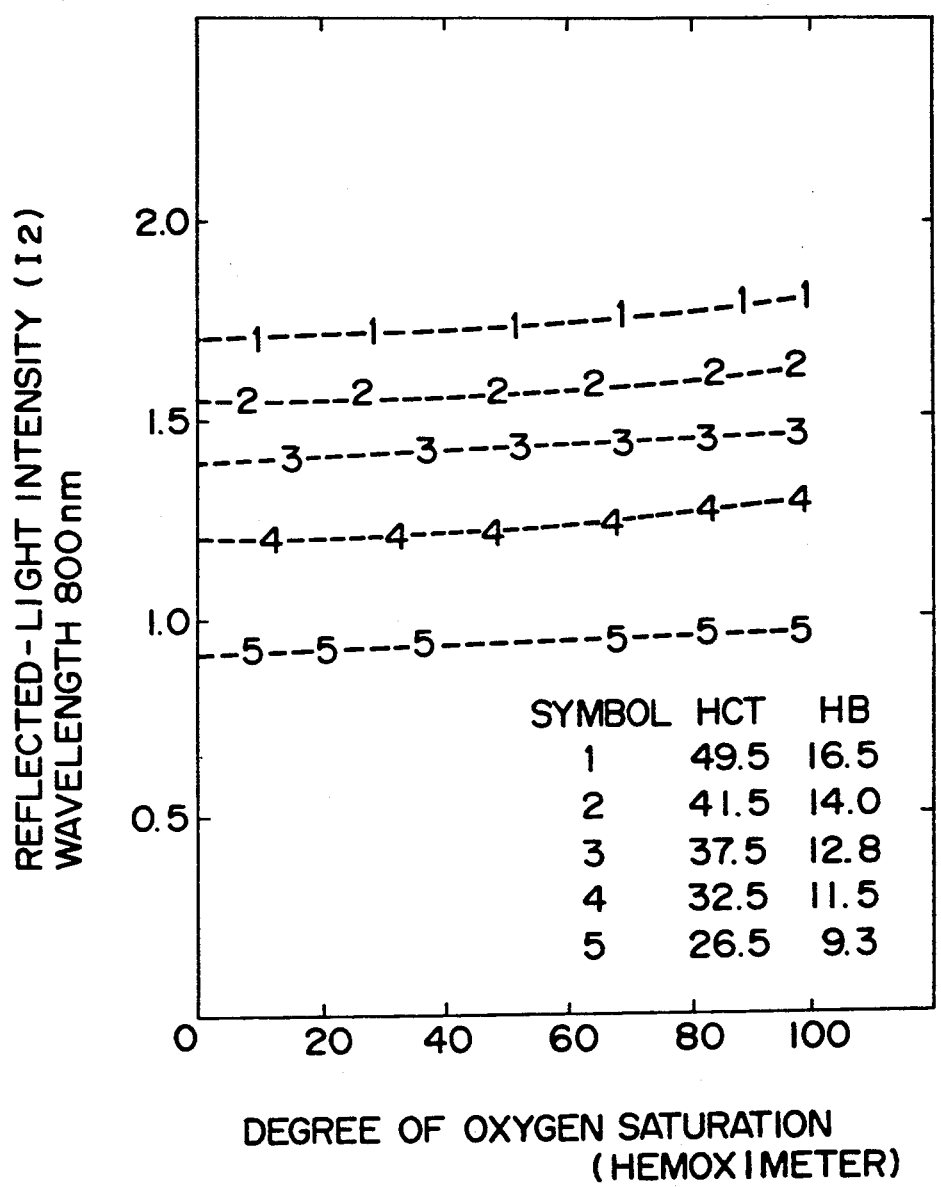
Figure 15:
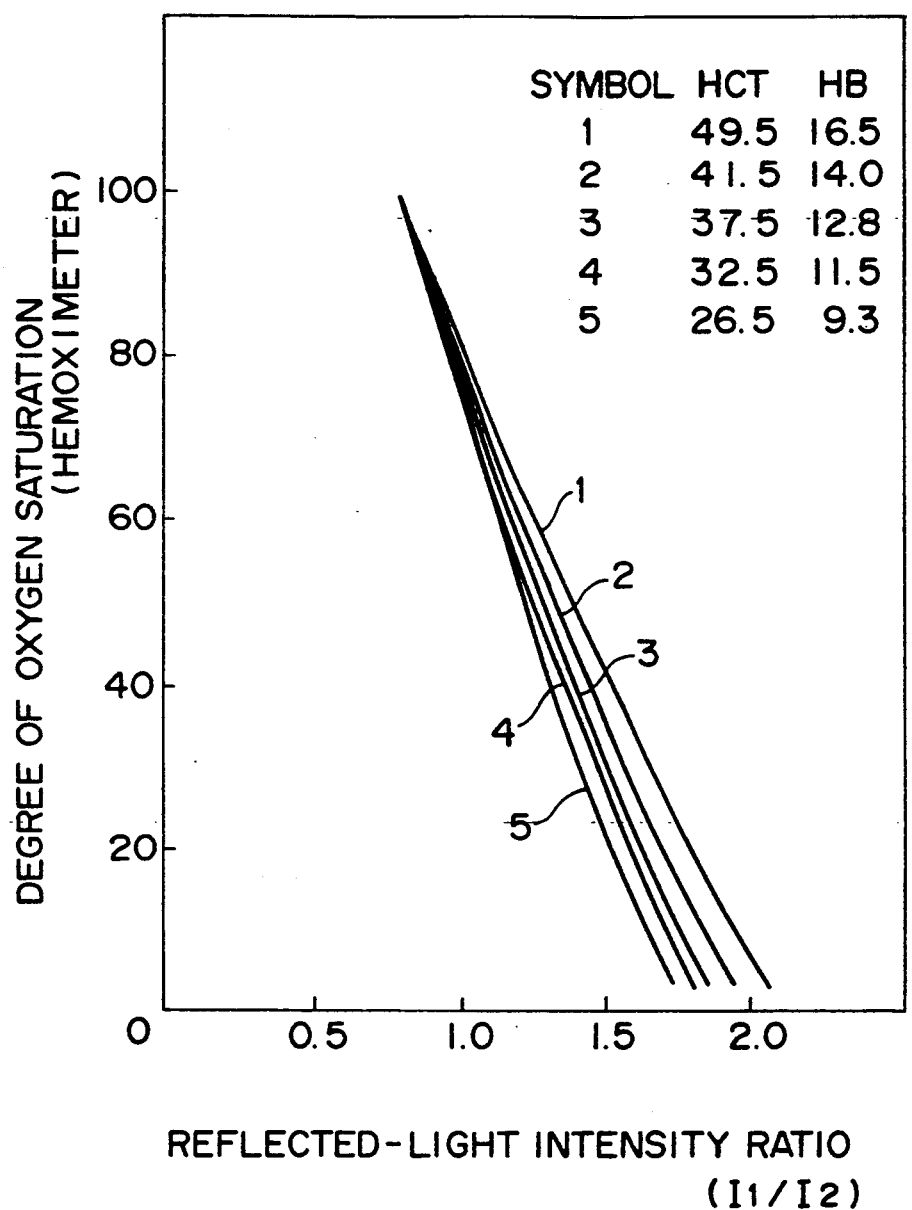
FIG. 15 is a diagram showing the relationship between degree of oxygen saturation obtained by a conventional method of measuring degree of oxygen saturation and degree of oxygen saturation measured by an OSM2 hemoxymeter for purposes of contrast.

As described above on the basis of FIG. 13, the light-absorption (reflection) characteristic of blood varies depending upon absorption and scattering due to pigments and particles in the blood, and the light-absorption coefficient varies greatly depending upon the state of bonding between hemoglobin and oxygen and the wavelength of the irradiating light. In particular, in the vicinity of a wavelength of 800 nm, $HbO_2$ and Hbr intersect and the extinction characteristics are equal.

Figure 21:
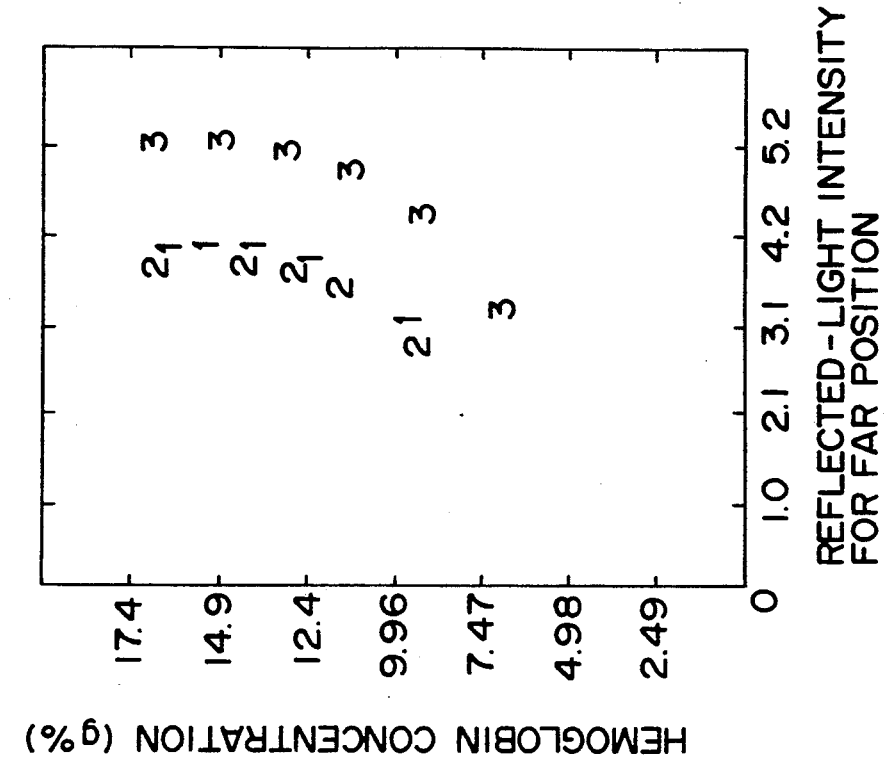
FIGS. 20 and 21 are diagrams in which is plotted the relationship between reflected-light intensity and hemoglobin concentration when blood is irradiated with light having a wavelength of about 800 nm, with distance being varied.
Figure 20:
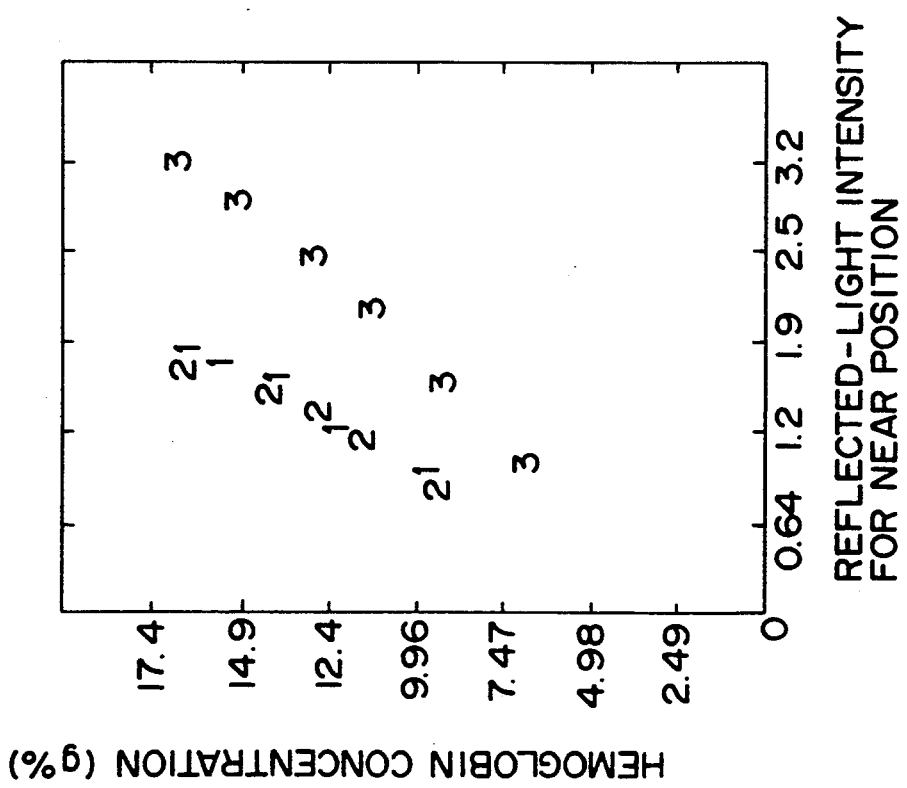

FIGS. 20 and 21 are plots showing the relationship between hemoglobin concentration and reflected-light intensity. These are experimental results regarding blood samples taken from three different bodies and using light of wavelength 800 nm. FIG. 20 shows results obtained where the distance between the received light and emitted light is 0.25 mm, and FIG. 21 shows results obtained where the distance between the received light and emitted light is 0.50 mm. It should be noted that these measurements of reflected-light intensity are results obtained upon previously calibrating each reflected-light intensity to a predetermined value using a white reflector.

Figure 22:
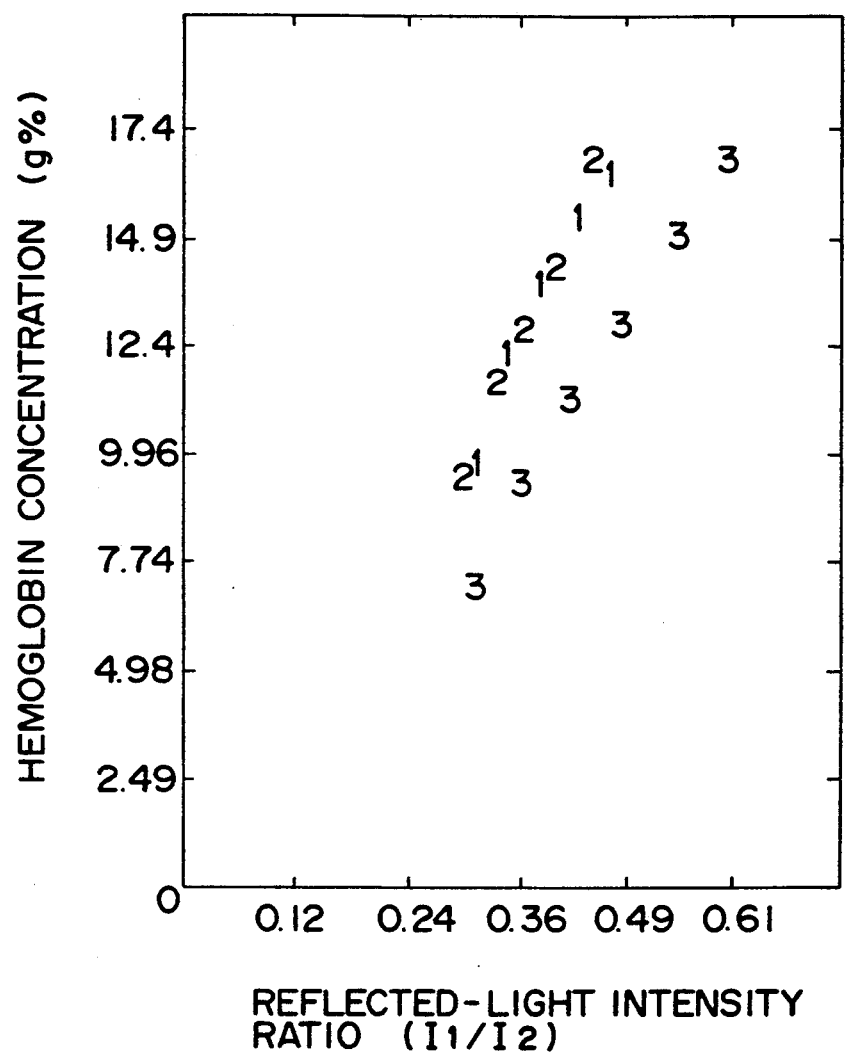
FIG. 22 is a diagram showing the relationship between a ratio $I_1/I_2$ and hemoglobin concentration, in which $I_1$ represents reflected-light intensity when the distance between received light and emitted light is 0.25 mm, and $I_2$ represents reflected-light intensity when the distance between received light and emitted light is 0.50 mm.

FIG. 22 shows the relationship between the ratio $I_1/I_2$ and hemoglobin concentration, where $I_1$ is the reflected-light intensity when the distance between the received light and emitted light is 0.25 mm, and $I_2$ is the reflected-light intensity when the distance between the received light and emitted light is 0.50 mm. FIGS. 20 and 21 show that each reflected-light intensity is considerably influenced by differences in blood. As shown in FIG. 22, however, this influence can be mitigated by taking the ratio of these intensities. Still, there is much influence from disparities in the scattering characteristic of blood.

Accordingly, the apparatus of the present invention is so adapted that the hemoglobin concentration of blood can be measured without the influence of differences among blood samples.

An apparatus for measuring hemoglobin concentration according to the present invention includes a light-irradiating circuit 100, a detecting unit 200 for detecting the intensity of light reflected from blood irradiated with light from the light-irradiating circuit 100, a correcting unit 300, a unit 400 for calculating hemoglobin concentration using the output of the correcting unit 300, and a display unit for displaying the output of the hemoglobin concentration calculating unit 400. Portions the same as those shown in FIG. 1 are designated by like reference characters.

The light-irradiating circuit 100 has a first light-irradiating unit and a second light-irradiating unit for irradiating the blood with light of a specific wavelength.

Figure 16:
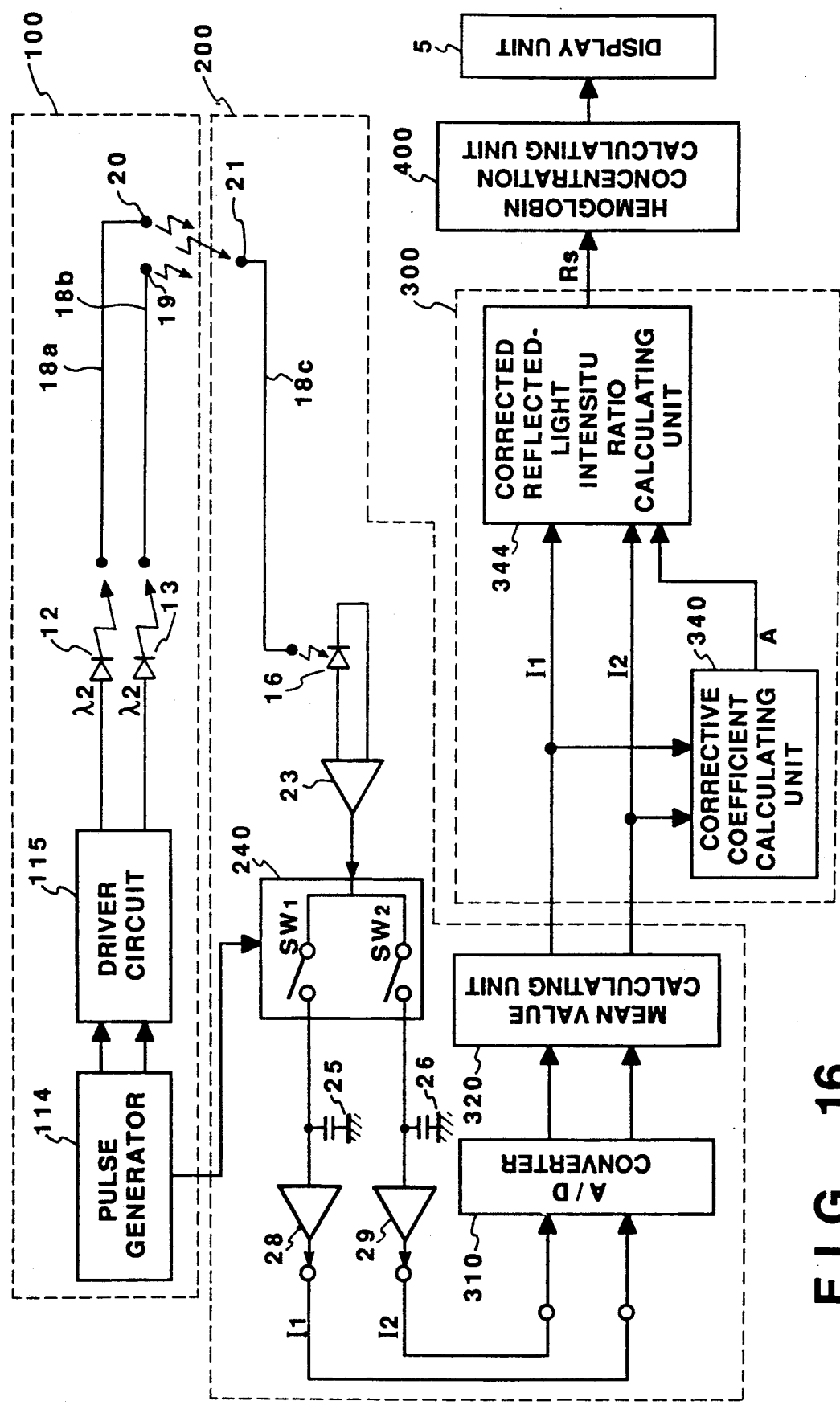
FIG. 16 is a block diagram of an apparatus for measuring hemoglobin concentration according to another embodiment of the invention.

In the arrangement shown in FIG. 16, the first light-irradiating unit and the second light-irradiating unit are constituted by a first light-emitting source for emitting light of the specific wavelength, a second light-emitting source for emitting light of the specific wavelength, and a light-irradiating unit for irradiating the blood with the light from each of the light-emitting sources.

More specifically, the light-irradiating circuit 100 comprises a light-emitting source and a light-irradiating unit for irradiating the blood with light from the light-emitting source. The light-emitting source comprises the two light-emitting diodes 12, 13 which emit light having a wavelength of about 800 nm ($\lambda_2$). The light-emitting diodes 12, 13 are arranged so as to emit light alternately by being driven through a driver circuit 115 to which pulses of a predetermined interval and pulse width are applied by a pulse generator 114 so as not to overlap in time. The light emitted by the light-emitting diode 12 passes through the light-emitting optical fiber 18a to irradiate the blood from the light-irradiating portion 20 formed by the end face of the optical fiber 18a. By adopting such an arrangement, the apparatus can be made small in size. Further, the light emitted by the light-emitting diode 13 passes through the light-emitting optical fiber 18b to irradiate the blood from the light-irradiating portion 19 formed by the end face of the optical fiber 18b.

The invention is not limited to the arrangement shown in FIG. 16, for it is permissible to adopt an arrangement in which the light-irradiating circuit is composed of a shared light-emitting source for emitting light of a specific wavelength, and two light-irradiating units for irradiating the blood from two different positions using the light from this light-emitting source.

The detecting unit 200 is for detecting the intensity of the light, which is emitted by the light-irradiating circuit 100, after the light is reflected from the blood. In the arrangement shown in FIG. 16, the photodetecting portion 21 of the detecting unit 200 is formed by the end face of the light-receiving optical fiber 18c and is so provided that the distance from the light-irradiating portion 19 differs from the distance from the light-irradiating portion 20.

The specific example of the sensor probe 50 having these light-irradiating portions 19, 20 and photodetecting portion 21 is as described above with reference to FIG. 2.

The detecting unit 200 has the photodiode 16 and the detecting amplifier 23 which receive the light detected by the photodetecting portion 21 and transmitted by the light-receiving optical fiber 18c. The photodiode 16 generates a current conforming to the intensity of the light signal. This current is converted into a voltage signal by the detecting amplifier 23. The detecting unit 200 has a signal separating circuit for separating the voltage signal from the detecting amplifier 23 into signals corresponding to the light-emission wavelengths of the light-emitting diodes 12, 13. The signal separating circuit is constituted by an analog switch 240, the capacitors 25, 26 and buffer amplifiers 28, 29.

The analog switch 240 has two switches SW1, SW2 turned "ON and "OFF" by a signal from the pulse generator 114. For example, when the light-emitting diode 12 emits light, the signal from the pulse generator 114 is applied to the analog switch 240 so that only SW1 assumes the "ON" state. As a result, the voltage signal from the detecting amplifier 23 is applied to the capacitor 25 to produce a mean signal voltage across the ends of the capacitor 25. This indicates the intensity of the reflected light of wavelength $\lambda_2$, in which the light is emitted by the light-emitting diode 12, irradiates the blood from the light-irradiating portion 20, is reflected from the blood and then received by the photodiode 16 via the photodetecting portion 21. The mean signal voltage is continuously outputted through the buffer amplifier 28 to form a signal $I_1$ indicative of reflected-light intensity. Similarly, a like operation is performed by a combination of the light-emitting diode 13, SW2 of the analog switch 240, capacitor 26 and buffer amplifier 29, whereby a signal $I_2$ indicative of the reflected-light intensity of wavelength $\lambda_2$ from light emitting diode 13 is outputted.

Further, the detecting unit 200 has processing means for the reflected-light intensity signals $I_1$, $I_2$ outputted by the signal separating circuit. The signal processing means has an analog-digital converter 310 for converting the reflected-light intensity signals $I_1$, $I_2$ into digital signals, and a mean value calculating unit 320 for computing mean values upon storing the digitized reflected-light intensity signals $I_1$, $I_2$ outputted by the analog-digital converter 310 a predetermined number (n) of times or within a predetermined period of time.

Figure 17:
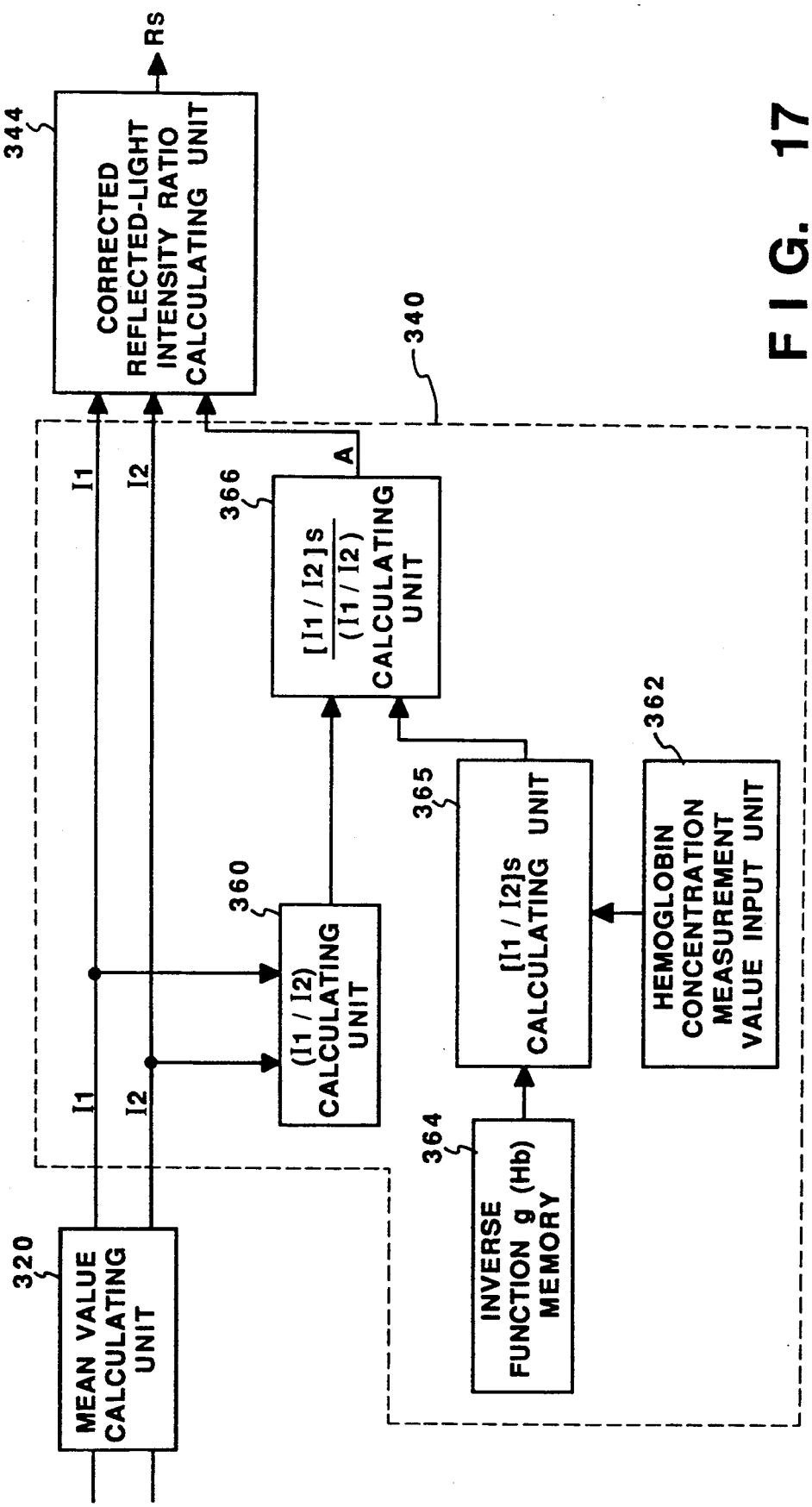
FIG. 17 is a block diagram showing a specific example of a corrective coefficient calculating unit in the block diagram of FIG. 16.

The correcting unit 300 has a corrective coefficient calculating unit 340, and a calculating unit 344 for computing a corrected reflected-light intensity ratio. As shown in FIG. 17, the corrective coefficient calculating unit 340 preferably comprises an arithmetic unit 360 for calculating a reflected-light intensity ratio ($I_1/I_2$) from one digitized reflected-light intensity signal $I_1$ and one digitized reflected-light intensity signal $I_2$ outputted by the mean value calculating unit 320, a measurement value input unit 362 for inputting a measurement value obtained by sampling blood and measuring the hemoglobin concentration of the blood, and a g(Hb) memory 364. Let $$h(R_s) = b_2 \cdot R_s^2 + b_1 \cdot R_s + b_0$$

represent the reference correlation function $h(R_s)$, which is a higher-order correlation curve (e.g., a second-degree regression curve) calculated from $I_1/I_2$, which is obtained from several kinds of blood of animal species and already measured, and from the hemoglobin concentration Hb. Here, for example, $$h(R_s) = -4.55 \cdot R_s^2 + 37.8 \cdot R_s - 4.91$$

[where $R_s = I_1/I_2$, and $h(R_s)$ is referred to as an Hb calibration curve hereinafter). The g(Hb) memory 364 stores the inverse function g(Hb) of the above, namely $$g(Hb) = 4.15 - \sqrt{16.18 - 0.22 \times h(R_s)}$$

The calculating unit further comprises an arithmetic unit 365 which uses the inverse function g(Hb) to calculate a reflected-light intensity ratio $[I_1/I_2]_s$ corresponding to the hemoglobin concentration inputted by the measurement value input unit 362, and an arithmetic unit 366 for calculating the corrective coefficient A in accordance with the following equation:

$$[I_1/I_2]_s/(I_1/I_2) \; (=A)$$

from $[I_1/I_2]_s$, which is outputted by the arithmetic unit 365, and $(I_1/I_2)$, which is outputted by the arithmetic unit 360.

The corrective coefficient A outputted by the corrective coefficient calculating unit 340 enters a corrected reflected-light intensity ratio calculating unit 344 along with the digitized reflected light-intensity signals $[I_1]$, $[I_2]$ continuously outputted by the mean value calculating unit 340. The calculating unit 344 computes the corrected reflected light-intensity ratio $R_s = A \times [I_1]/[I_2]$ from the abovementioned signals.

In other words, the correcting unit 300 obtains the value of the ratio of (reflected-light intensity ratio calculated from reference correlation function) to (measured reflected-light intensity ratio) with regard to a known hemoglobin concentration, namely $$\frac{\text{(reflected-light intensity ratio calculated from reference correlation function)}}{\text{(measured reflected-light intensity ratio)}}$$

and thereafter multiplies the successively measured reflected-light intensity ratio by the value of this ratio, which serves as a corrective coefficient. Thus, a so-called span calibration is performed based on the known hemoglobin concentration.

The hemoglobin concentration calculating unit 400 stores the reference correlation function $h(R_s)$ $$h(R_s) = b_2 \cdot R_s^2 + b_1 \cdot R_s + b_0$$

which is a higher-order correlation curve (e.g., a second-degree regression curve) calculated from $I_1/I_2$, which is obtained from several kinds of blood of animal species and already measured, and from the hemoglobin concentration Hb. Here, for example, $$h(R_s) = -4.55 \cdot R_s^2 + 37.8 \cdot R_s - 4.91$$

[where $R_s = I_1/I_2$, and $h(R_s)$ is referred to as an Hb calibration curve hereinafter). The unit 400 calculates hemoglobin concentration, using the abovementioned equation of the Hb calibration curve, from the corrected reflected-light intensity ratio RS outputted by the calculating unit 344.

The signal outputted by the hemoglobin concentration calculating unit 400 is displayed by the display unit 5. It will suffice if the latter is means capable of providing an external indication of the measured value. Well-known means can be used, such as a cathode ray tube, printer, liquid-crystal display unit or recorder.

A method of measuring the hemoglobin concentration by the hemoglobin concentration measuring apparatus of the present invention will now be described in accordance with an embodiment with reference to the flowchart of FIG. 18.

Figure 18:
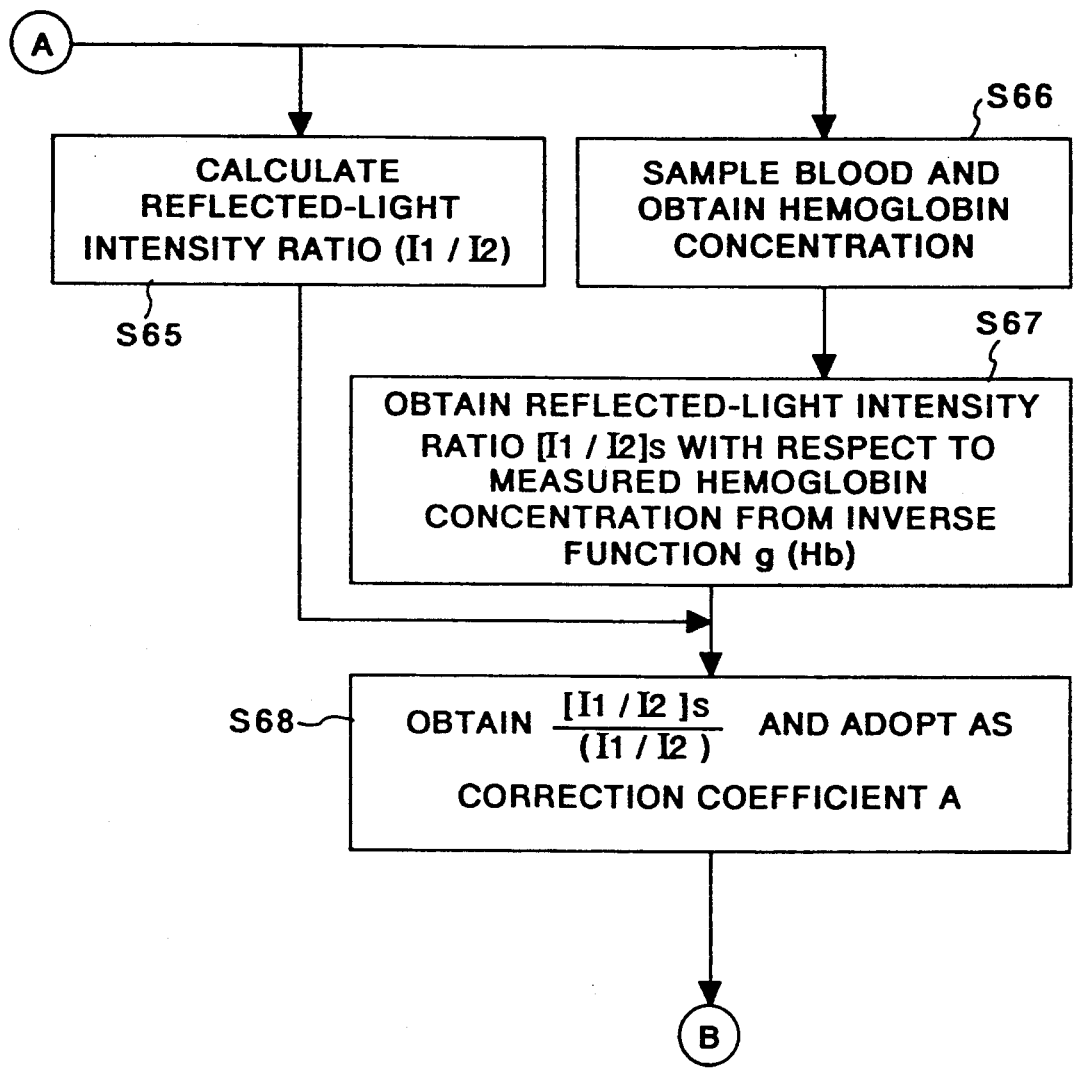
FIG. 18A and 18B are flowcharts showing a method of measuring hemoglobin concentration by an apparatus for measuring hemoglobin concentration according to an embodiment of the invention.

In accordance with the embodiment shown in FIG. 18, a connector of the configuration shown in FIG. 3 to which the sensor probe of FIG. 2 has been mounted is attached to a blood circuit at a step S61. Next, at step S62, blood is successively irradiated with the light of the approximate wavelength of 880 nm ($\lambda_2$) from the light-irradiating portions 19, 20 formed by the end face of the optical fiber of the light-irradiating unit shown in FIG. 16, and the intensity of light reflected from the blood irradiated with each light beam from the light-irradiating unit 100 is detected n times by the detecting unit 200. At step S63, the mean value of each reflected-light intensity detected n times is calculated and the digitized reflected-light intensity signals $I_1$, $I_2$ are outputted.

It is determined at step S64 whether to apply a correction to the hemoglobin concentration. The program proceeds to step S69 when the correction is not carried out. When the correction is performed, however, the program proceeds to steps S65 and S66. At step S65, the reflected-light intensity ratio ($I_1/I_2$) is calculated from one (the initially outputted) of each of the digitized reflected-light intensity signals $I_1$, $I_2$ outputted at step S63.

At step S66, blood to be judged is sampled to measure hemoglobin concentration. The program then proceeds to step S67 to calculate the reflected-light intensity ratio $[I_1/I_2]_s$ corresponding to the measured hemoglobin concentration from the inverse function g(Hb) of the reference correlation function $h(R_s)$ $$h(R_s) = b_2 \cdot R_s^2 + b_1 \cdot R_s + b_0$$

which is a higher-order correlation curve (e.g., a second-degree regression curve) calculated from the reflected light-intensity ratio ($I_1/I_2$), which is obtained from several kinds of blood of animal species and already measured, calculated and stored, and from the hemoglobin concentration Hb. Here, for example, $$h(R_s) = -4.55 \cdot R_s^2 + 37.8 \cdot R_s - 4.91$$

[where $R_s = I_1/I_2$, and $h(R_s)$ is referred to as an Hb calibration curve hereinafter). Thus the inverse function g (Hb) is $$g(Hb) = 4.15 - \sqrt{16.175 - 0.2198 \times h(R_s)}$$

When the reflected-light intensity ratio ($I_1/I_2$) is thus obtained, the program proceeds to step S68. Here, from $[I_1/I_2]$ outputted at step S65 and $[I_1/I_2]_s$ outputted at step S66, the corrective coefficient $([I_1/I_2]_s)/(I_1/I_2)$ (=A), which is the ratio between the two, is calculated.

It is determined at step S69 whether the corrective coefficient A calculated at step S68 is to be used. If it is decided that the corrective coefficient A is to be used, the program proceeds to step S70, at which the corrected reflected-light intensity ratio $R_s$ is obtained from $R_s = A \times [I_1]/[I_2]$ using the coefficient and the digitized reflected-light intensity signals $[I_1]$, $[I_2]$ outputted continuously at step S63. If the corrective coefficient A calculated at step S68 is cot to be used, then the program proceeds to step S71, at which the reflected-light intensity ratio R is obtained from $R = [I_1]/[I_2]$ using the digitized reflected-light intensity signals $[I_1]$, $[I_2]$ outputted continously at step S63.

Next, at step S72, using the corrected reflected-light intensity ratio $R_s$ obtained at step S70 or the reflected-light ratio $R_s$ obtained at step S71, hemoglobin concentration is calculated using the reference correlation function $h(R_s)$ $$h(R_s) = b_2 \cdot R_s^2 + b_1 \cdot R_s + b_0$$

which is a higher-order correlation curve (e.g., a second-degree regression curve) calculated from $I_1/I_2$, which is obtained from several kinds of blood of animal species and already measured, calculated and stored, and from the hemoglobin concentration Hb. Here, for example, $$h(R_s) = -4.55 \cdot R_s^2 + 37.8 \cdot R_s - 4.91$$

[where $R_s = I_1/I_2$, and $h(R_s)$ is referred to as an Hb calibration curve hereinafter).

The hemoglobin concentration outputted at step S72 is displayed at step S73, and it is determined at step S74 whether to terminate measurement. If measurement is not terminated, the program returns to step S62 and the foregoing measurement is repeated.

Figure 19:
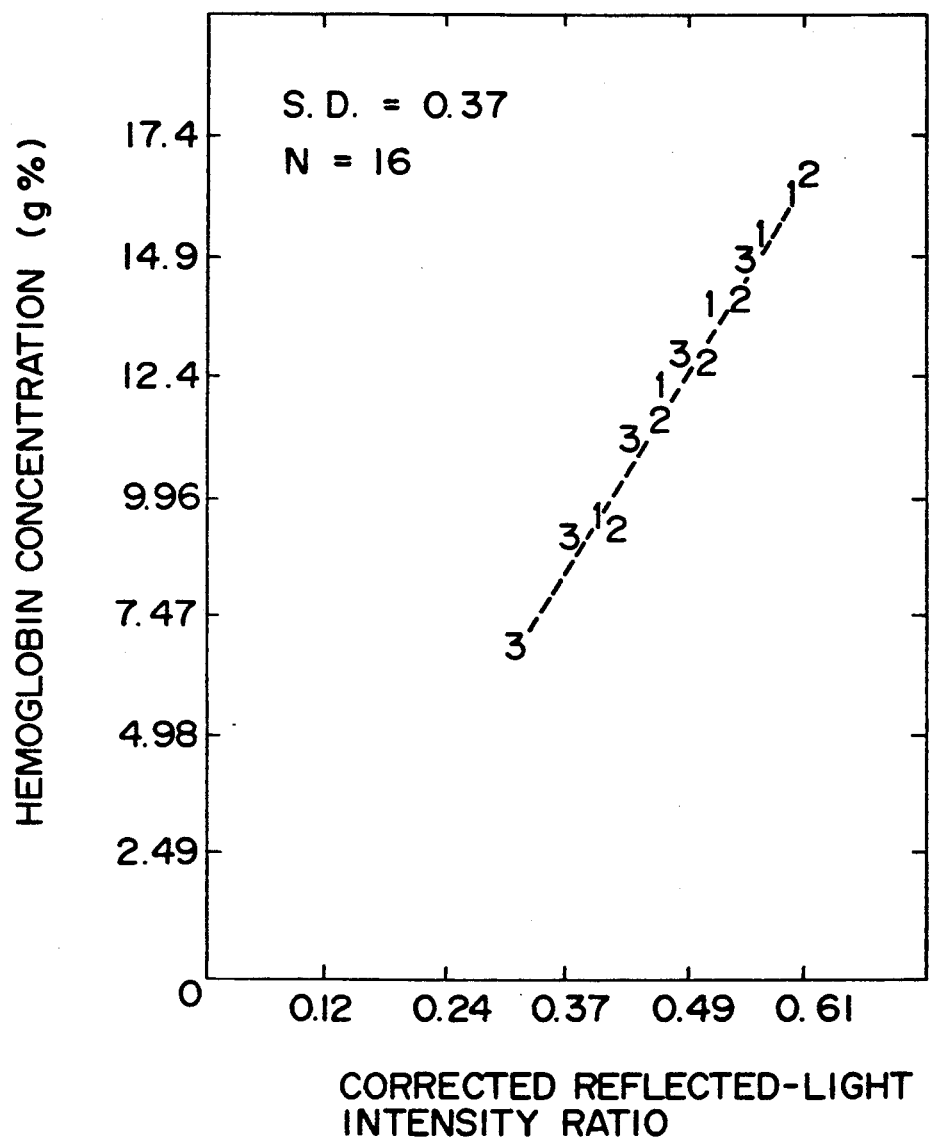
FIG. 19 is a diagram showing a extinction characteristic of hemoglobin measured by an OSM2 hemoxymeter for purposes of contrast with hemoglobin concentration obtained by an embodiment of the apparatus for measuring hemoglobin concentration according to the present invention.

FIG. 19 illustrates the relationship between hemoglobin concentration obtained according to the embodiment and hemoglobin concentration measured with an OSM2 hemoximeter (manufactured by Radiometer) used for purposes of contrast. It was found from these results that accurate measurement can be carried out, in which the value (x) of hemoglobin concentration obtained in accordance with the method of this embodiment approximates a correlation coefficient = 1 (y = x), with respect to the value (y) of hemoglobin concentration obtained using the OSM2 hemoximeter, with the error (S.D.) also being sufficiently small.

INDUSTRIAL APPLICABILITY

Thus, as set forth above, the apparatus for measuring hemoglobin concentration and the apparatus for measuring degree of oxygen saturation of the present invention are suited to continuous measurement of hemoglobin concentration in blood and degree of oxygen saturation of hemoglobin.

What is claimed is:

1. An apparatus for measuring a degree of oxygen saturation in blood, comprising:

source means for emitting light at a first and second wavelength ($\lambda_1$, $\lambda_2$), with a difference of a degree of extinction between oxygenated hemoglobin and carbomonoxy hemoglobin being comparatively large at said first wavelength and small at said second wavelength;

first light-irradiating means having a first light-irradiating portion, and being coupled to said source means for alternately irradiating blood with light of said first or second wavelength ($\lambda_1$, $\lambda_2$);

second light irradiating means having a second light-irradiating portion, and being coupled to said source means for constantly irradiating the blood with light of said second wavelength $\lambda_2$;

detecting means, arranged such that the distance from the detecting means to said first light-irradiating means and the distance from the detecting means to said second light-irradiating means differ, for detecting intensities ($I_1$, $I_2$, $I_3$) of light reflected from the blood irradiated with the light from each of the first and second light-irradiating portions of said first and second light-irradiating means corresponding to their wavelength;

memory means for storing an Hb calibration curve;

arithmetic means for calculating a reflected-light intensity ratio function g(Hb') of blood having a reference value (Hb') of hemoglobin concentration by reference to said Hb calibration curve stored in said memory means;

first corrective value calculating means for calculating a first corrective value (X) based on both a reflected-light intensity ratio $(I_2/I_3)_s$ from a blood with known hemoglobin concentration and said reflected-light intensity ratio function, according to an equation $X = g(Hb') \times (I_2/I_3)/(I_2/I_3)_s$, to correct a ratio ($I_2/I_3$) of detected reflected-light intensity ($I_2$) due to irradiation with light of said second wavelength produced by said first light-irradiating means versus detected reflected-light intensity ($I_3$) due to irradiation with light of said second wavelength produced by said second light-irradiating means;

second corrective values calculating means for calculating a second corrective value ($C_1$) based on said first corrective value (X), the reflected-light intensity ($I_3$) of light from the second light-irradiating means detected continuously by said detecting means, and a constant value ($C_0$), according to an equation $C_1 = C_0 \times (I_3) \times (X)$;

reflected-light intensity ratio correcting means for correcting to remove an influence of hematocrit value and for calculating a corrected reflected-light intensity ratio ($R_s$) based on said second corrective value ($C_1$), a reflected-light intensity ratio ($I_1/I_2$) of the detected reflected-light intensity ($I_1$) of light of said first wavelength produced by the first light-irradiating means versus detected reflected-light intensity ($I_2$) of light of said second wavelength produced by the first light-irradiating means, according to an equation $R_s = (I_1 - C_1)/(I_2 - C_1)$; and oxygen saturation degree calculating means for calculating the degree of oxygen saturation in blood based on a correlation function (f(x)) using the corrected reflected light intensity ratio ($R_s$) outputted by said reflected light intensity ratio correcting means.

2. An apparatus for measuring a degree of oxygen saturation according to claim 1, wherein said memory means stores a reference correlation function h(x) as said Hb calibration curve: wherein $$h(x) = b_2 x^2 + b_1 x + b_0$$

and where $x = I_2/I_3$, and $b_0$, $b_1$ and $b_2$ are constant values.

3. An apparatus for measuring a degree of oxygen saturation according to claim 1, wherein said second corrective means calculates said second value $C_1$ by using an equation:

$$C_1 = C_0 \times (I_3) \times (X)$$

where $C_0$ is a constant value.

4. An apparatus for measuring a degree of oxygen saturation according to claim 1, wherein said oxygen degree calculating means calculates the degree of oxygen saturation in blood based on the correlation function f(x):

$$f(x) = a_3 R_s^3 + a_2 R_s^2 + a_1 R_s + a_0$$

where $a_0$, $a_1$, $a_2$ and $a_3$ are constant values.

5. An apparatus for measuring a degree of oxygen saturation according to claim 1, wherein each of said first and second light-irradiating means includes an optical fiber for transmitting light from said source means respectively to said first and second light-irradiating portions, each of said first and second light-irradiating portions comprising an end face of said optical fiber.

6. An apparatus for measuring a degree of oxygen saturation according to claim 1, wherein said detecting means includes a photodetector, and a light-transmitting portion for transmitting light from a photodetecting portion to said photodetector, said photodetecting portion comprising an end face of an optical fiber which forms the light-transmitting portion.

7. An apparatus for measuring hemoglobin concentration in blood, comprising:

source means for emitting light at a specific wavelength ($\lambda_2$), with a difference of a degree of extinction between oxygenated hemoglobin and carbomonoxy hemoglobin being comparatively small;

first and second light-irradiating means having first and second light-irradiating portions, respectively, and being coupled respectively to said source means for irradiating blood with light of said specific wavelength ($\lambda_2$) from different directions;

detecting means, arranged such that the distance from the detecting means to said first light-irradiating means and the distance from the detection means to said second light-irradiating means differ, for detecting intensities ($I_1/I_2$) of light reflected from the blood irradiated with the light from the first and second light-irradiating portions of said first and second light-irradiating means;

corrective coefficient calculating means for calculating a corrective coefficient (A) based on a ratio of a ratio ($I_1/I_2$) of the reflected-light intensity ($I_1$) of light from said first light-irradiating means to the reflected-light intensity ($I_2$) of light from said second light-irradiating means to a ratio (($I_1/I_2$)$_s$) of intensities of reflected-light from a blood with known hemoglobin concentration irradiated by said first and second light-irradiating means, according to an equation $A=((I_1/I_2)_s/(I_1/I_2))$;

reflected-light intensity ratio correcting means for multiplying a reflected-light intensity ratio $(I_1/I_2)$ by said corrective coefficient (A) to obtain a corrected reflected-light ratio $(R_s)$; and hemoglobin concentration calculating means for calculating the hemoglobin concentration in blood based on a correlation function $h(R_s)$ using the corrected reflected-light intensity ratio $(R_s)$ outputted by said reflected light intensity ratio correcting means.

8. An apparatus for measuring a hemoglobin concentration according to claim 7, wherein each of said first and second light-irradiating means has different light-irradiating portions for irradiating the blood with light from said source means from different directions.

9. An apparatus for measuring a hemoglobin concentration according to claim 7, wherein said corrective coefficient calculating means includes memory means for storing an inverse function g(HB), and arithmetic means for calculating a reflected-light intensity ratio $((I_1/I_2)_s)$ from blood with known hemoglobin concentration using both the inverse function g(Hb) and a reference value of hemoglobin concentration.

10. An apparatus for measuring a hemoglobin concentration according to claim 7, wherein said reflected-light intensity ratio correcting means calculates said corrected reflected-light intensity ratio (Rs) according to an equation:

$$Rs = A \times (I_1/I_2) = \{(I_1/I_2)_s/(I_1/I_2)\} \times (I_1/I_2).$$

11. An apparatus for measuring a hemoglobin concentration according to claim 7, wherein said hemoglobin concentration calculating means calculates the hemoglobin concentration in blood based on the correlation function:

$$H(Rs) = -4.55\, R_s^2 + 37.8\, R_s - 4.91.$$

12. An apparatus for measuring a hemoglobin concentration according to claim 7, wherein said detecting means includes a photodetector, and a light-transmitting portion for transmitting light from a photodetecting portion to said photodetector, said photodetecting portion comprising an end face of an optical fiber which forms the light-transmitting portion.

* * * * *

UNITED STATES PATENT AND TRADEMARK OFFICE
CERTIFICATE OF CORRECTION

PATENT NO. : 5,149,503

DATED : September 22, 1992

INVENTOR(S) : KOHNO et al

It is certified that error appears in the above-identified patent and that said Letters Patent is hereby corrected as shown below:

Column 5, line 39, following the words "The best", insert --mode--.

Column 16, line 28, following the words "display unit", insert --5--.

Column 20, line 18, delete "cot".

Signed and Sealed this

Seventh Day of December, 1993

*Attest:*

BRUCE LEHMAN

*Attesting Officer*     *Commissioner of Patents and Trademarks*